United States Patent [19]

Oddsen et al.

[11] Patent Number: 4,944,443
[45] Date of Patent: Jul. 31, 1990

[54] SURGICAL SUTURING INSTRUMENT AND METHOD

[75] Inventors: Robert R. Oddsen, Centerport; Ralph Ger, Lake Success, both of N.Y.

[73] Assignee: Innovative Surgical Devices, Inc., Westbury, N.Y.

[21] Appl. No.: 185,054

[22] Filed: Apr. 22, 1988

[51] Int. Cl.⁵ .............................................. A61B 17/00
[52] U.S. Cl. .................................. 227/19; 227/901; 606/219
[58] Field of Search ........ 128/334 R; 227/19, DIG. 7

[56] References Cited

U.S. PATENT DOCUMENTS

| 641,036 | 1/1900 | Pilling . |
|---|---|---|
| 2,011,169 | 8/1935 | Wappler . |
| 2,034,785 | 3/1936 | Wappler . |
| 2,384,697 | 9/1945 | Riccardi . |
| 3,585,985 | 6/1971 | Gould . |
| 3,882,854 | 5/1975 | Hulka et al. . |
| 4,038,987 | 8/1977 | Komiya . |
| 4,049,002 | 9/1977 | Kletschka et al. . |
| 4,122,856 | 10/1978 | Mosior et al. . |
| 4,235,238 | 11/1980 | Ogiu et al. . |
| 4,257,419 | 3/1981 | Goltner et al. . |
| 4,273,129 | 6/1981 | Boebel . |
| 4,424,810 | 1/1984 | Jewusiak . |
| 4,485,953 | 12/1984 | Rothfuss . |
| 4,595,007 | 6/1986 | Mericle . |
| 4,784,137 | 11/1988 | Kulik et al. .................. 227/19 X |

FOREIGN PATENT DOCUMENTS

| 293929 | 9/1916 | Fed. Rep. of Germany . |
|---|---|---|
| 2330182 | 1/1975 | Fed. Rep. of Germany . |
| 2553540 | 6/1977 | Fed. Rep. of Germany . |
| 8300615 | 3/1983 | PCT Int'l Appl. . |
| 8505025 | 11/1985 | PCT Int'l Appl. .......... 227/DIG. 1 |

OTHER PUBLICATIONS

Ger, Ralph, "The Management of Certain Abdominal Herniae by Intra-Abdominal Closure of the Neck of the Sac", Annals of the Royal College of Surgeons of England, pp. 342–344, Sep. 1982.

*Primary Examiner*—Paul A. Bell
*Attorney, Agent, or Firm*—Rosen, Dainow & Jacobs

[57] ABSTRACT

A surgical instrument for suturing a hernial opening in internal body tissues of a patient comprises an elongate staple cartridge rotatably mounted to an elongate frame at a distal end thereof and an elongate staple forming plate movably mounted to the frame for ejecting a staple from the cartridge into the body tissues of the patient and deforming the staple from an open position to a closed position in which the staple holds together two pieces of body tissue on opposite sides of the hernial opening. The instrument further includes a rotator assembly operatively connected to the cartridge for rotatating the cartridge from an orientation aligned with the frame means to a staple ejection orientation transverse to the frame. A tissue positioning assembly separate from the staple forming plate is provided for gripping, approximating and temporarily holding together in a stapling position the two pieces of body tissue prior to and during a stapling operation.

58 Claims, 14 Drawing Sheets

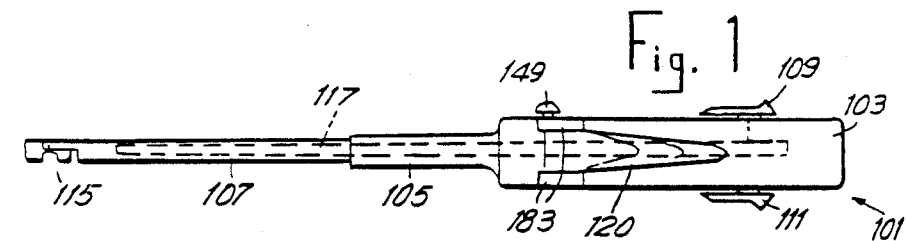
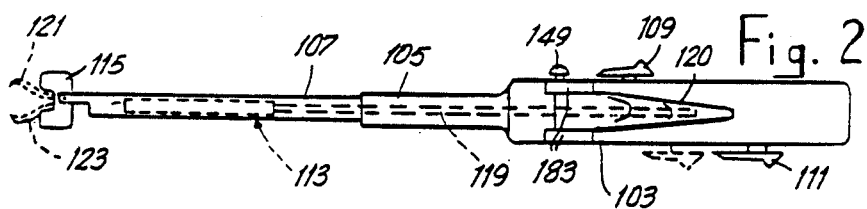
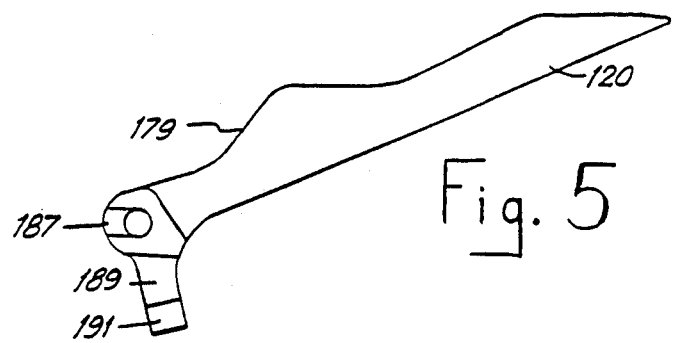
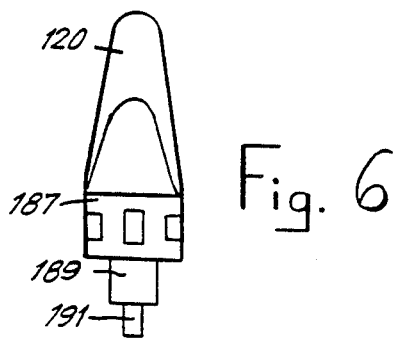

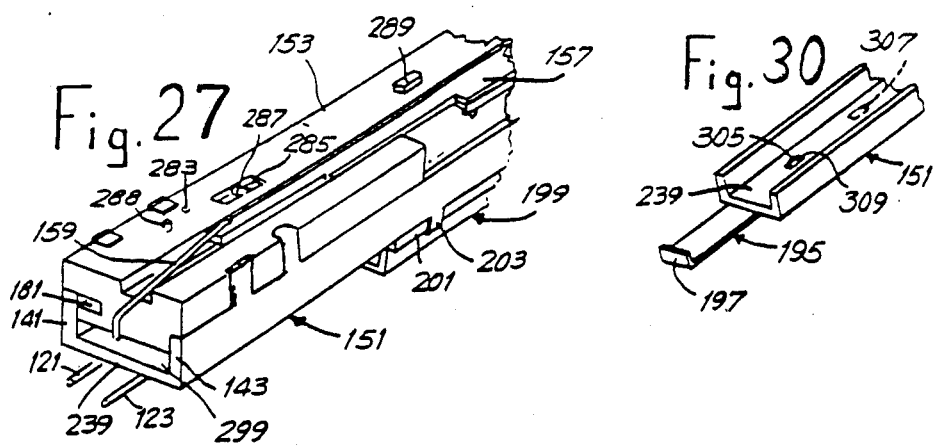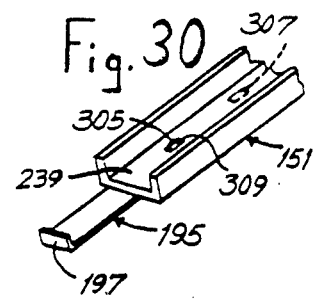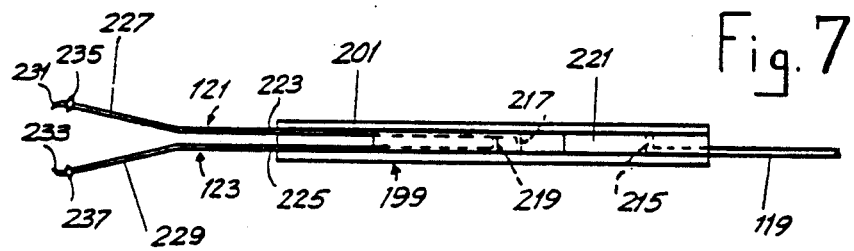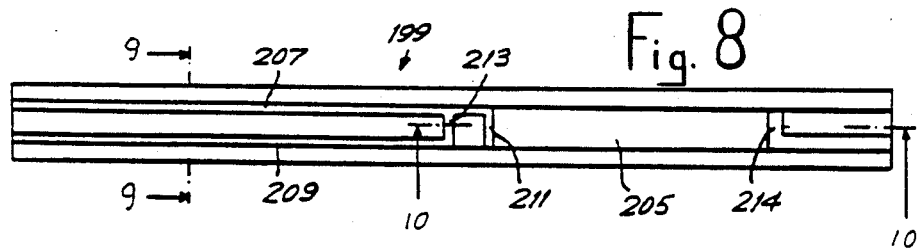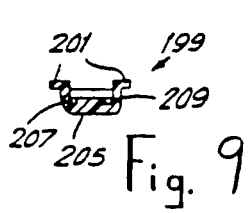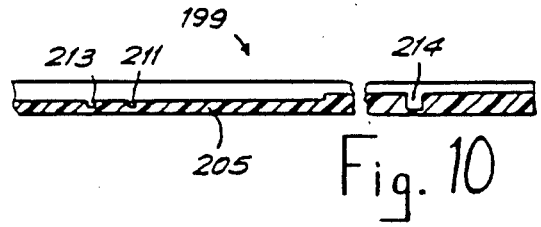

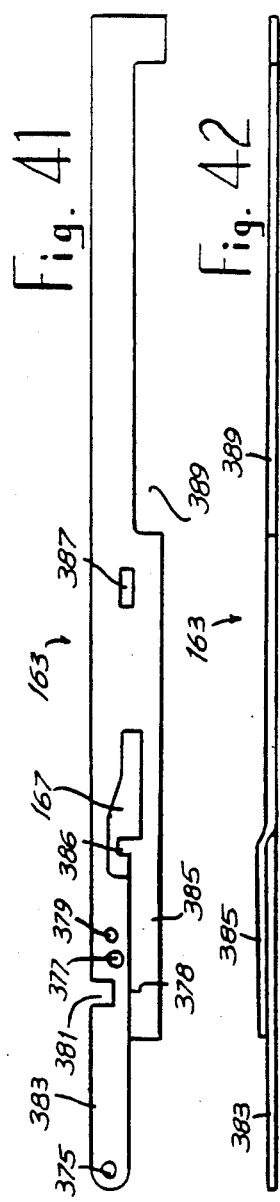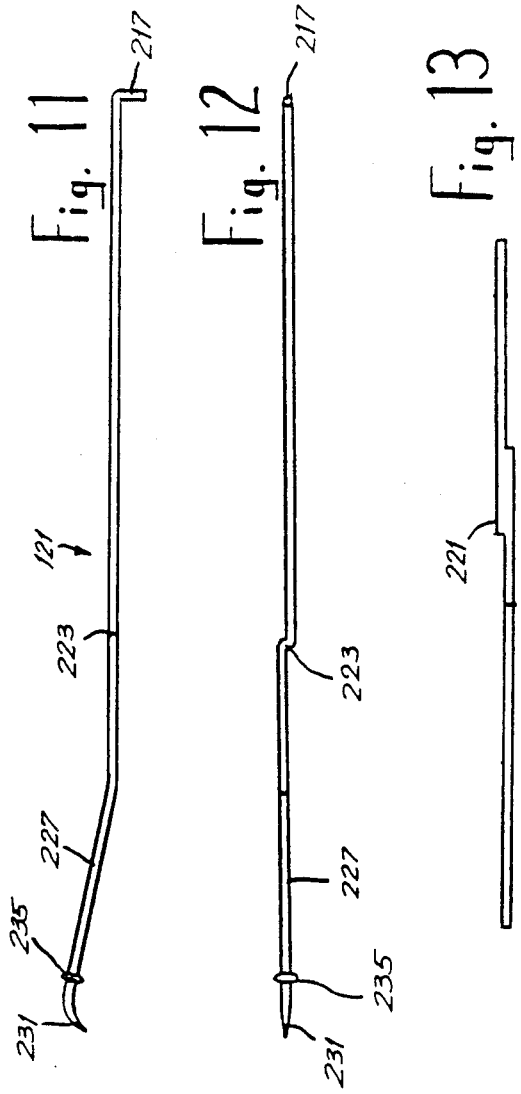

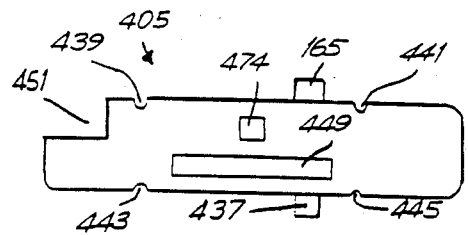
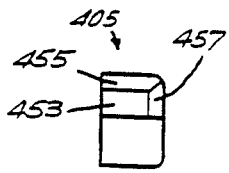
Fig. 53
Fig. 56
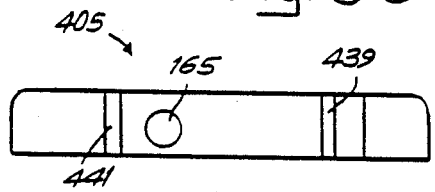
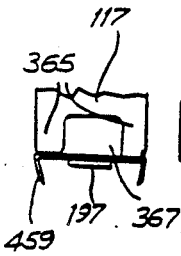
Fig. 54
Fig. 64
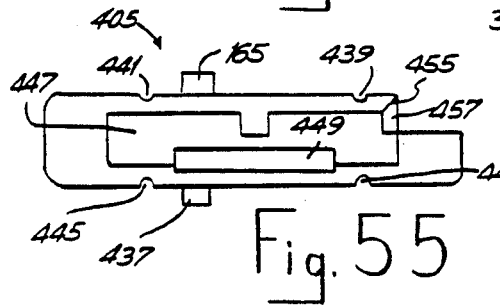
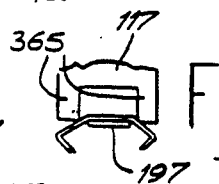
Fig. 55
Fig. 65
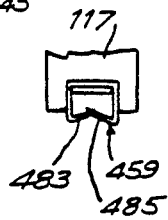
Fig. 66
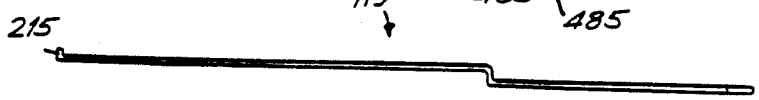
Fig. 14
Fig. 15

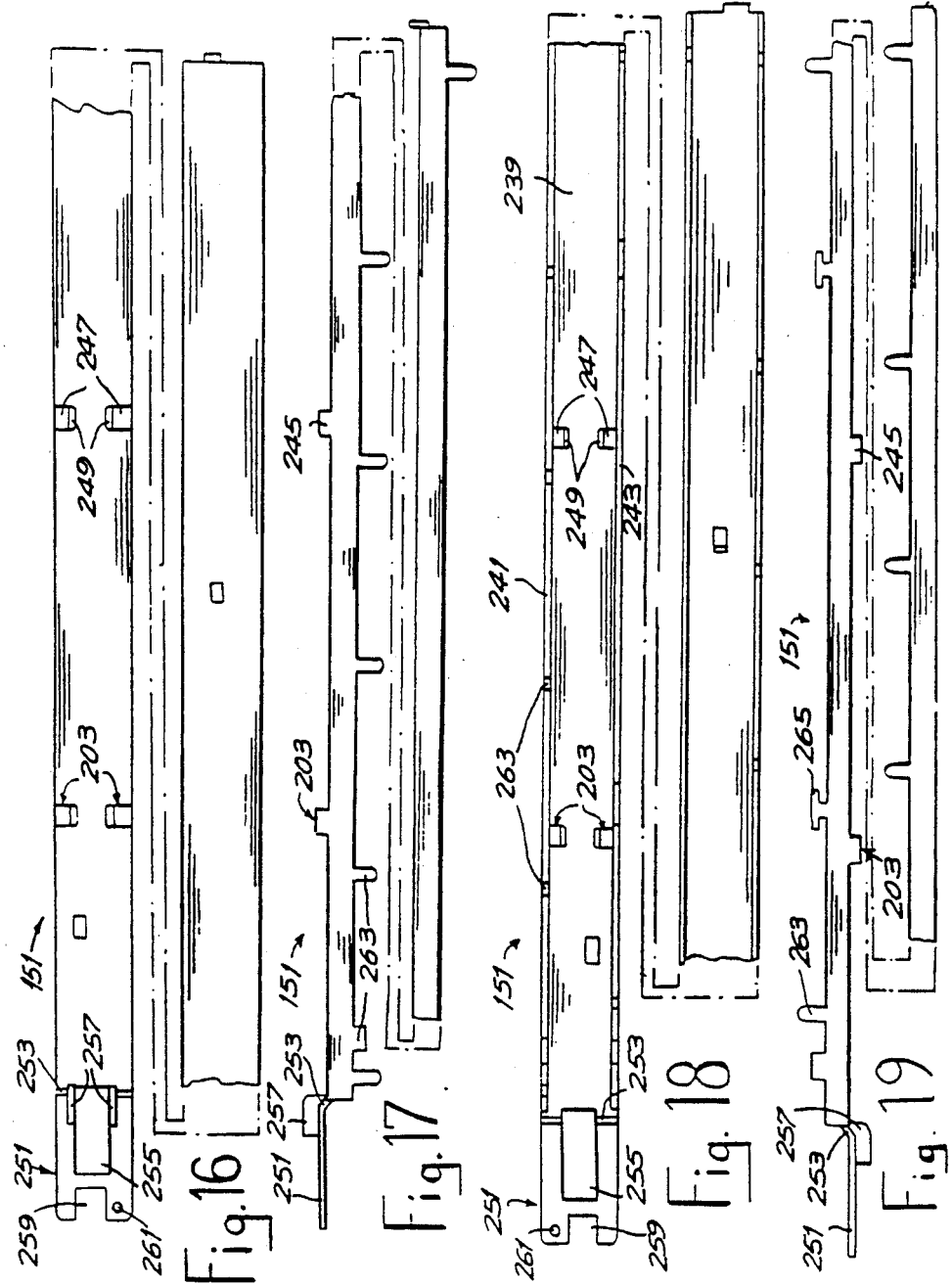

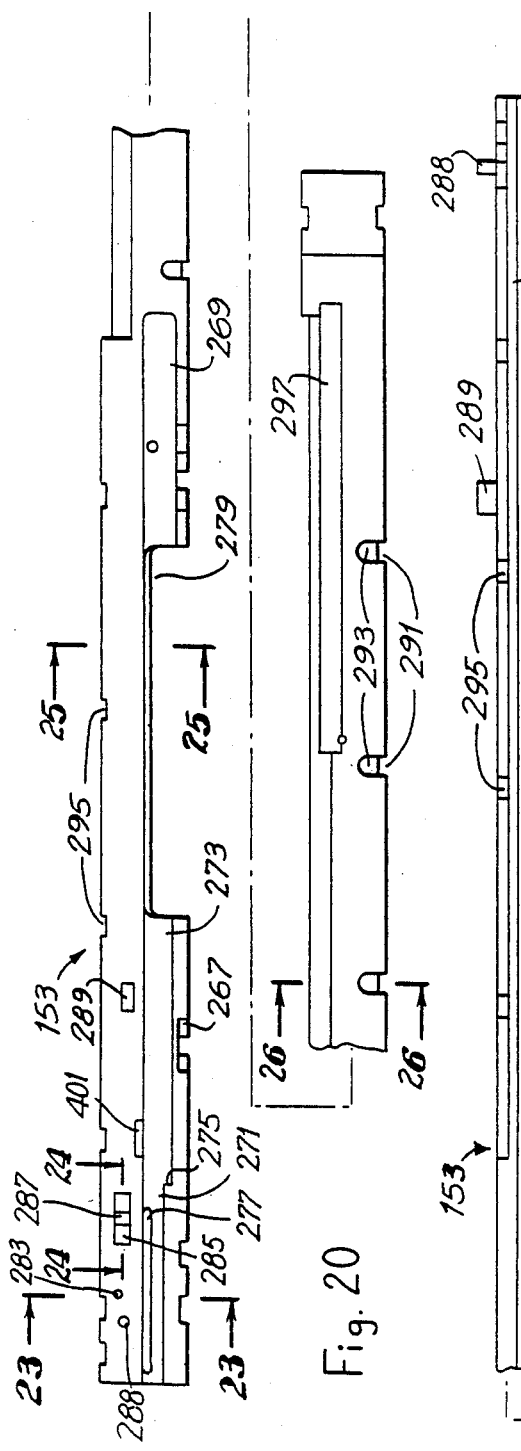
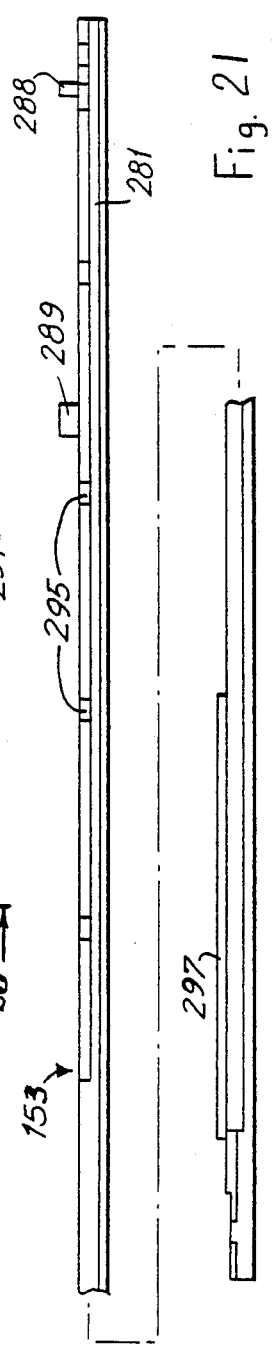
Fig. 20
Fig. 21
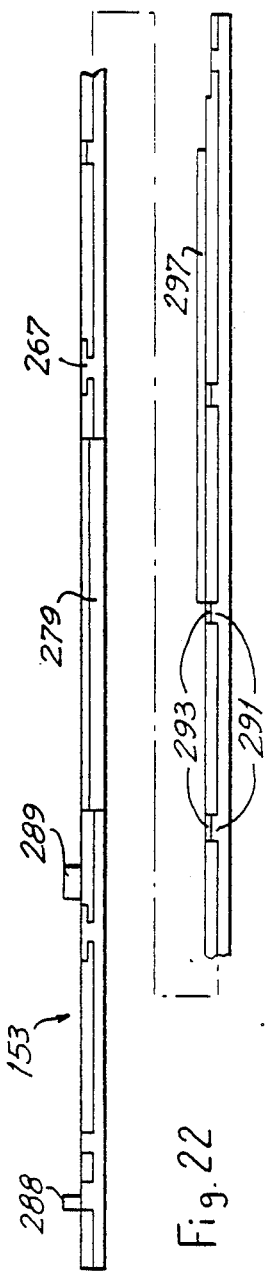
Fig. 22

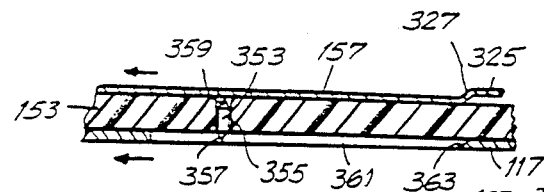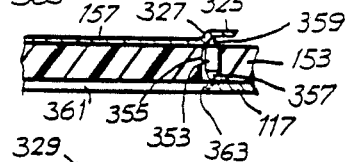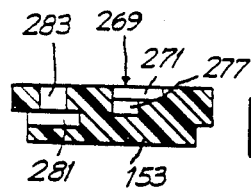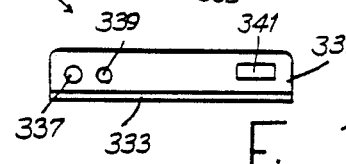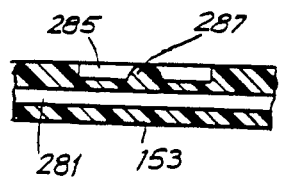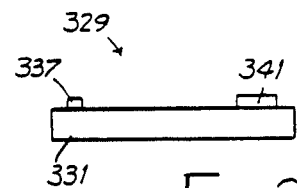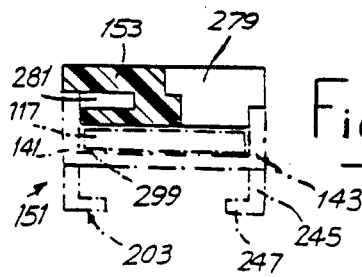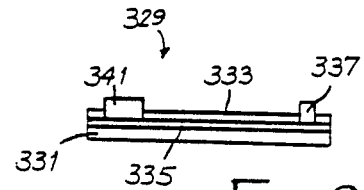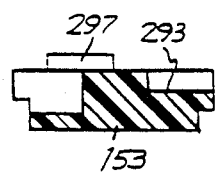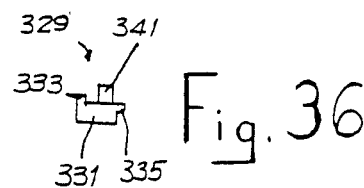

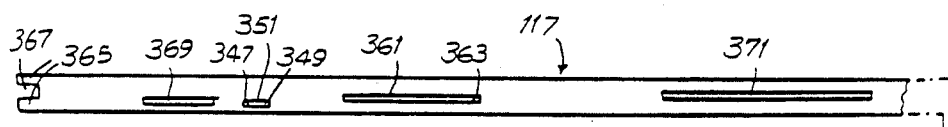
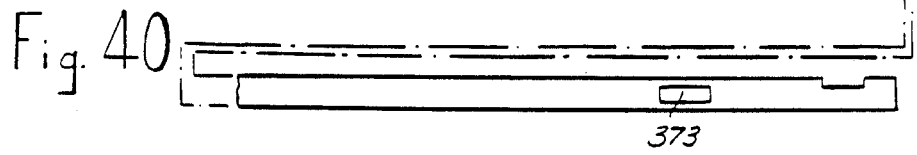
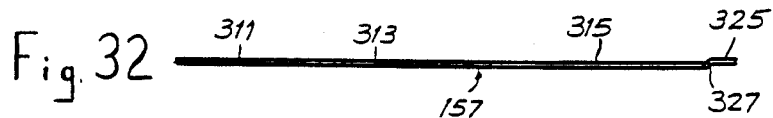
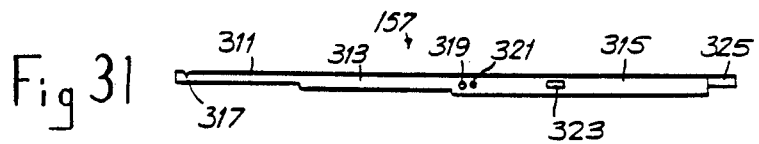
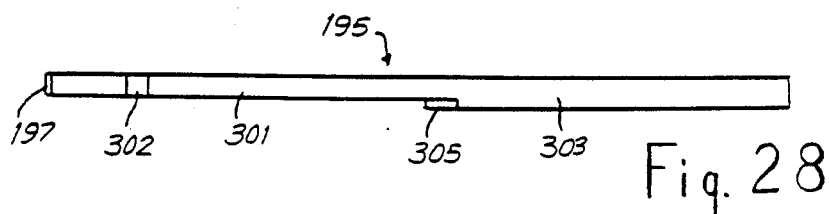
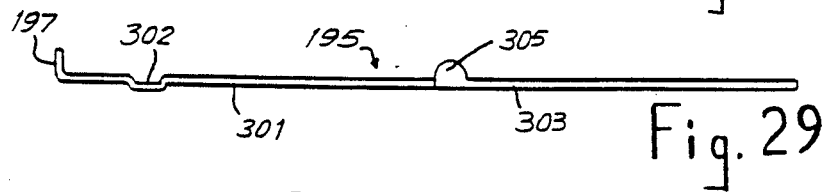
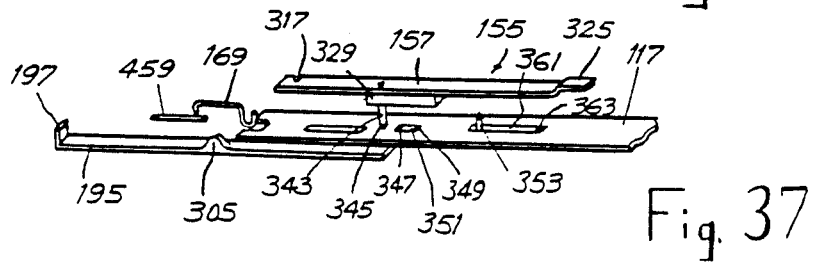

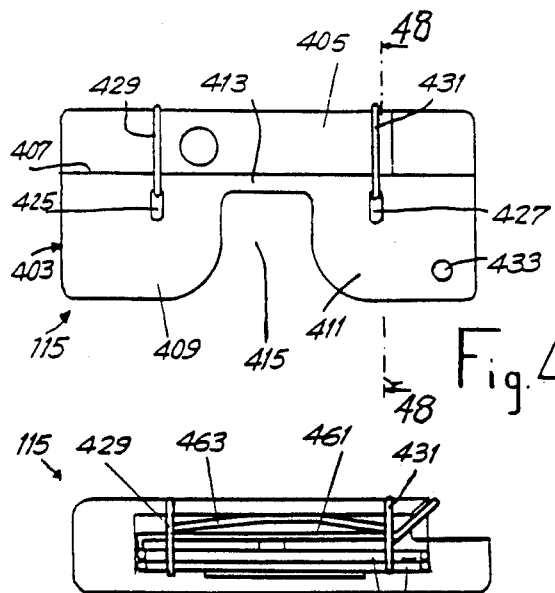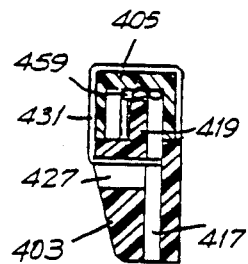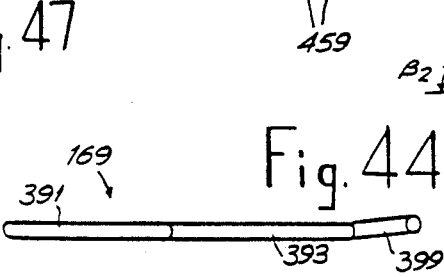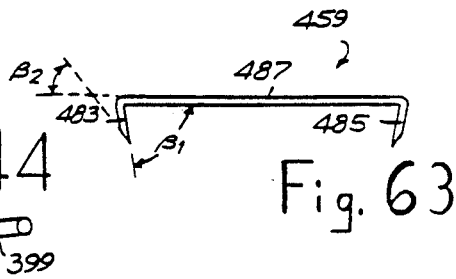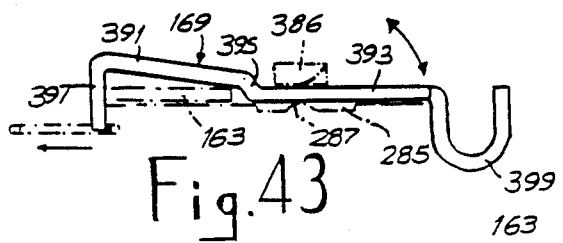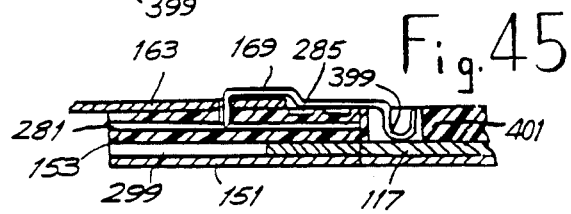

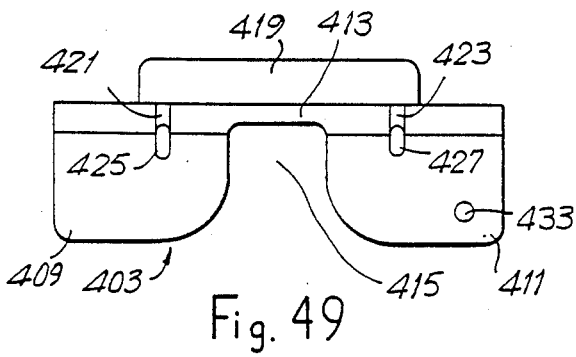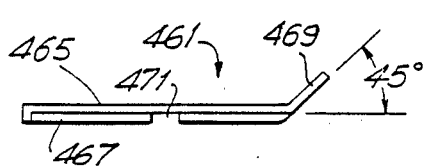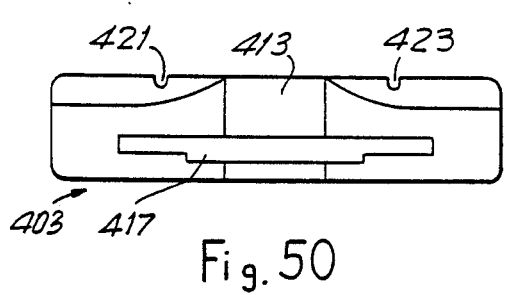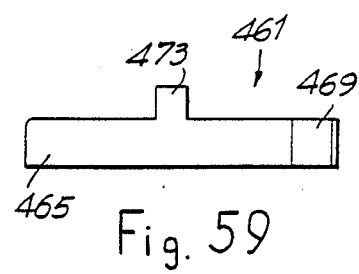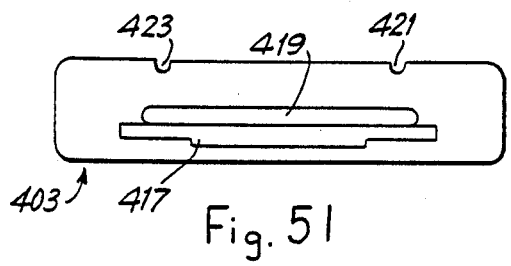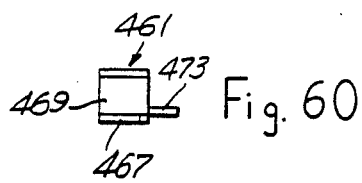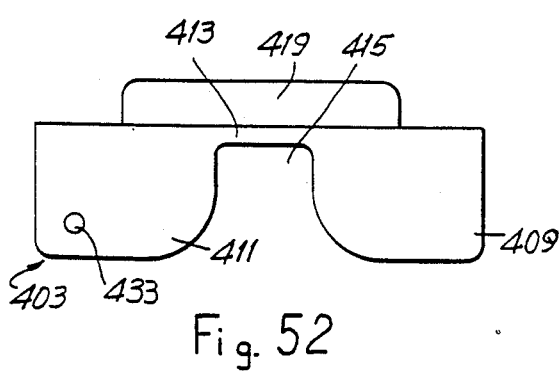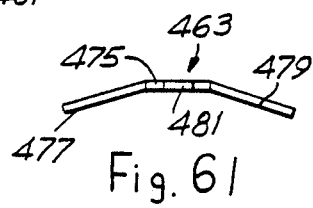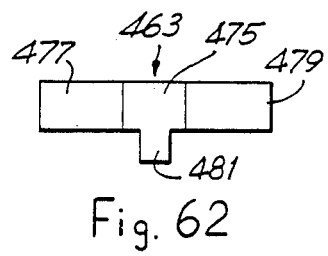

SURGICAL SUTURING INSTRUMENT AND METHOD

BACKGROUND OF THE INVENTION

This invention relates to a surgical instrument and an associated method for closing an internal opening in a patient from within the body cavity. The instrument and method are especially useful in performing corrective surgery for hernias, particularly those where the hernial sac descends towards the scrotum, commonly known as an indirect or congenital hernia.

In hernias, frequently a portion of the intestine enters the hernial sac. Conventional corrective surgery for such hernias entails a surgical incision of approximately 5 to 6 inches in the groin. Several layers of the abdominal wall are divided to reach the hernia. The hernia is then closed outside the abdominal wall in a manner resembling the tying of a sack at its neck.

The performance of such conventional corrective surgery causes severe physical trauma to the operative area and emotional trauma to the patient. Also the scrotal contents of the patient may be handled and complications may arise, namely testicular atrophy. Many other complications are possible: those related to any incision, such as bleeding and infection, and those related to a traditional hernia operation, such as damages to bowel and bladder, nerves and large blood vessels. In addition, cutting through so many layers of tissue may severely traumatize the tissue and upset the patient's emotional equilibrium. Other disadvantages of conventional hernia surgerY are the long recuperation time and the large unsightly scar.

OBJECTS OF THE INVENTION

An object of the present invention is to provide an instrument and an associated method for performing corrective surgery on internal wounds such as hernias where invasion of the patient's body tissues is minimized and resultant trauma is reduced.

Another more particular object of the present invention is to provide such an instrument and method wherein the size of surgical incision in the patient's body tissues is minimized.

Yet another particular object of the present invention is to provide in hernia cases an instrument and method for performing corrective surgery in which handling of a patient's scrotum and contents is avoided.

Another object of the present invention is to provide such a surgical instrument which can be inserted into the body cavity of the patient through a site on the patient's body remote from the wound.

A further particular object of the present invention is to provide such an instrument and method wherein the surgical operation is performed from within the body cavity of the patient, i.e., on the inner side of the hernia.

SUMMARY OF THE INVENTION

A surgical instrument for closing an opening, particularly a hernia, in the internal body wall of a patient from within the body cavity of the patient comprises, in accordance with the present invention, an elongate frame or superstructure, a staple storage component on the frame for temporarily storing at least one staple, a staple forming and ejection assembly at least in part movably mounted to the frame for ejecting the staple from the staple storage component into the body tissues of the patient and deforming the staple from an open position to a closed position in which the staple holds together two pieces of body tissue on opposite sides of the opening. In one embodiment of the present invention, the instrument further comprises a tissue positioning assembly separate from the staple forming and ejection assembly for gripping, approximating and temporarily holding together in a stapling position the two pieces of body tissue prior to and during a stapling operation. In approximating the two pieces of tissue, the positioning assembly juxtaposes the tissue edges to one another and ensures that the tissue pieces lie in the same plane. Preferably, the tissue positioning assembly is designed to hold the two pieces of tissue in compression during the stapling operation. Proper approximation and tight pressing of the tissues against one another ensures a successful closure and reduces the chances of scarring.

In another embodiment of the present invention, the staple storage component includes an elongate staple cartridge rotatably mounted to the frame at a distal end thereof and a rotator assembly operatively connected to the cartridge for rotating the cartridge from an orientation aligned with the frame to a staple ejection orientation transverse to the frame. The rotator assembly is critical in allowing large staples to pass through a small opening in the abdominal wall.

A first actuator is at least in part movably mounted to the frame and connected to the staple forming and ejection assembly for moving at least a portion thereof, while a second actuator separate from the first actuator is provided for moving at least a portion of the tissue positioning assembly prior to the stapling operation, the second actuator being at least in part movably mounted to the frame and connected to the tissue positioning assembly.

Pursuant to another feature of the present invention, the cartridge includes a staple chamber and spring tines for preventing a staple from falling out of the chamber prior to a staple ejection operation. In addition, the cartridge is advantageously provided with an inlet opening, a biasing spring and a staple plate for enabling the reception and storage of additional staples by the cartridge subsequently to the stapling operation.

Pursuant to another feature of the present invention, the rotator assembly includes a rotator member slidably mounted to the frame for longitudinal motion therealong and a rotator link pivotably attached at one end to the cartridge and at an opposite end to the rotator member. The instrument further comprises a timing mechanism mounted to the frame for controlling the initation and duration of motion of the rotator member. In a preferred embodiment of the present invention, the staple forming and ejection assembly includes an elongate plate element movably mounted to the frame, the timing mechanism including a slot formed in the elongate plate element and a pin on the rotator member coacting with the slot.

In accordance with further, particular, features of the present invention, the rotator assembly further includes a biasing spring for forcing the pin against the elongate plate element and coacting stop elements are provided on the rtator member and the frame for limiting a range of longitudinal motion of the rotator member and concomitantly limiting the range of rotational motion of the cartridge. Advantageously, the slot in the elongate plate element is formed with beveled ends and the pin on the rotator member has a substantially conically shaped free end, whereby the pin is compelled to move transversely out of the slot upon an arresting of forward longitudinal motion of the rotator member by the coacting stop elements.

The coacting stop elements may include a floating pin slidably mounted to the frame for controlled movement in a direction transverse thereto, a shoulder at a proximal end of the rotator member and an additional slot in the elongate plate element, the additional slot being formed with a beveled proximal end and the floating pin being provided with conically shaped ends. In such a motion limiting structure, the floating pin is forced in a camming type motion transversely out of the slot upon an engagement of the floating pin with the beveled proximal end of the additional slot during relative motion of the elongate plate element and the rotator member after termination of a cartridge rotation operation. As a result of the transverse motion, the floating pin is shifted into a locking engagement with the shoulder of the rotator member.

Pursuant to an additional feature of the present invention, the staple forming and ejection assembly includes an anvil member with an anvil flange projecting, during the stapling operation, into a staple forming plane intersecting the cartridge. The surgical instrument further comprises a shifting mechanism for moving the anvil flange away from the staple forming plane prior to a cartridge rotation operation. Preferably, the anvil member is an elongate member with a proximal end attached to the frame and a distal end carrying the anvil flange, the shifting mechanism including a camming projection on the anvil member engageable with the plate member of the staple forming and ejection assembly.

Pursuant to yet another feature of the present invention, the frame carries a staple storage magazine in addition to the staple storage cartridge. A loading mechanism is provided for shifting additional staples from the storage magazine into the cartridge, and a staple arrest device is attached to the frame for preventing motion of staples from the magazine into the cartridge during a cartridge rotation operation and the stapling operation. The staple magazine preferably takes the form of an elongate chamber in the frame and the loading mechanism includes a compression spring. Moreover, the staple arrest device includes a pivotably mounted catch member having a camming portion engageable with the plate element.

In accordance with yet a further feature of the present invention, the tissue positioning assembly includes a pair of tong-like gripper members mounted to the frame for longitudinal motion therealong and a camming element for changing the distance between the tong-like gripper members during motion thereof so that during a closing stroke the tissue positioning assembly simultaneously draws two pieces of body tissue together and towards the staple cartridge. Preferably, the second actuator is mechanically connected to the tong-like gripper members and is spring biased for urging the tong-like gripper members towards a closed configuration. The tong-like gripper members are advantageously provided with collar-like elements for limiting the degree that the tong-like gripper members may be inserted into the body tissues of a patient and for ensuring the alignment of the tissue pieces in the same plane during an approximating operation.

A method for suturing an opening, such as a hernial tear, in the internal body tissues of a patient comprises, in accordance with the present invention, the steps of (a) making a small incision through the external body wall of the patient at a site on the patient's body remote from the opening in the internal body wall of the patient, (b) inserting an elongate suturing instrument through the incision, and (c) moving the instrument through the incision and through an internal body cavity of the patient so that the distal end of the instrument is close to the opening in the internal body wall of the patient while remaining on the body cavity side of the opening. In another step, the two pieces of body tissue are gripped, on opposite sides of the opening, approximated and held together, the step of gripping occurring from the internal side of the opening. The composite step of gripping, approximating and holding is performed with the suturing instrument by manual manipulation at a proximal end thereof. In another step of a method in accordance with the present invention, the two pieces of body tissue are stapled together, the step of stapling being performed from the internal side of the opening and by manual manipulation of the instrument at a proximal end thereof.

Pursuant to another feature of the present invention, a staple-storing cartridge at a distal end of the suturing instrument is rotated upon insertion of the instrument through the incision into the body cavity. The step of rotating is being accomplished via manual manipulation at the proximal end of the instrument.

The composite step of gripping, approximating and holding advantageously includes the steps of inserting ends of tong-like gripper members into the two pieces of tissue and moving the tong-like gripper members towards one another and towards the distal end of the suturing instrument. The composite step of gripping, approximating and holding is accomplished by manipulation of a first mechanism of the instrument, including the tong-like gripper members, and the step of stapling is accomplished by manipulation of a second mechanism of the instrument separate and distinct from the first mechanism.

Pursuant to yet another feature of the present invention, the distal end of a laproscope is inserted into the body cavity to provide for visual inspection of the opening and the distal end of the instrument during a stapling operation. Preferably, the laproscope is inserted through an opening in the body wall of the patient different from the incision through which the suturing instrument is inserted.

The suturing instrument and the associated surgical method in accordance with the present invention minimize the number and sizes of incisions necessary to effect hernial repair, thereby greatly reducing the physical and emotional trauma of hernia patients. The incisions are made at a distance from the site of the hernia, which further decreases the trauma to that area. Because of the substantial reduction in trauma, as well as a corresponding decrease in complications, patients operated on with an instrument in accordance with the present invention can walk away from the hospital an hour after surgery. In contrast, patients treated with conventional procedures must remain hospitalized for days, or longer in cases where complications arise.

It is to be noted that the rotatability of the staple cartridge enables the alignment of the cartridge with the longitudinal axis of the instrument and concomitantly enables an insertion of the narrow side of the cartridge first through the incision, thereby decreasing the minimum required size of the incision. The rotatability of the staple cartridge thus allows the use of larger staples without an increase in the size of the incision through which the surgical instrument is inserted.

Other advantages of the present invention include the possibility of using a local anesthetic rather than a general anesthetic, an increase in the efficiency and ease of the operation and a concomitant reduction in support staff and operating time.

BRIEF DESCRIPTION OF THE DRAWING

FIG. 1 is a partially schematic side elevational view, on a reduced scale, of a surgical instrument in accordance with the present invention for suturing an opening, particularly a hernial tear, in internal body tissues of a patient, showing a staple cartridge in a longitudinal or aligned orientation.

FIG. 2 is a side elevational view similar to FIG. 1, showing the stable cartridge in a rotated orientation.

FIG. 5 is a side elevational view of an actuator lever on a handle portion of the instrument of FIGS. 1-4.

FIG. 6 is a front elevational view of the actuator lever of FIG. 5.

FIG. 7 is a top view, on an enlarged scale, of a tissue positioning assembly shown in part in FIGS. 2 and 4.

FIG. 8 is a top view, on a larger scale, of a housing component of the positioning assembly of FIG. 7.

FIG. 9 is a cross-sectional view taken along line 9—9 in FIG. 8.

FIG. 10 is a partial longitudinal cross-sectional view taken along line 10—10 in FIG. 8.

FIG. 11 is a top view, on a substantially enlarged scale, of a tong-like gripper member shown in FIG. 7.

FIG. 12 side elevational view of the tong-like gripper member in FIG. 11.

FIG. 13 side elevational view of a cover plate included in the tissue positioning assembly of FIG. 7.

FIG. 14 is a top view, on a reduced scale, of a tissue positioning assembly actuator rod shown in part in FIGS. 3 and 7.

FIG. 15 is a side elevational view of the actuator rod of FIG. 14.

FIG. 16 is a bottom view, on an enlarged scale, of a channel member partially illustrated in FIGS. 3 and 4.

FIG. 17 is a side elevational view of the channel member of FIG. 16, taken from below in that drawing figure.

FIG. 18 is a top view of the channel member of FIGS. 16 and 17.

FIG. 19 is a side elevational view of the channel member of FIGS. 16–18, taken from below in FIG. 18.

FIG. 20 is a top view, on an enlarged scale, of a plastic body member partially illustrated in FIGS. 3 and 4.

FIG. 21 is a side elevational view of the plastic body member of FIG. 20, taken from above in that drawing figure.

FIG. 22 is a side elevational view of the plastic body member of FIG. 20, from below in that drawing figure.

FIG. 23 is a cross-sectional view taken along line 23—23 in FIG. 20.

FIG. 24 is a cross-sectional view taken along line 24—24 in FIG. 20.

FIG. 25 is a cross-sectional view taken along line 25—25 in FIG. 20.

FIG. 26 a cross-sectional view taken along line 26—26 in FIG. 20.

FIG. 27 is a perspective view, on an enlarged scale, of a portion of the surgical instrument at a distal end thereof.

FIG. 28 a top view, on an enlarged scale, of an anvil member shown in FIG. 4

FIG. 29 is a side elevational view of the anvil member of FIG. 28.

FIG. 30 a perspective view of a distal end of the channel member of FIG. 16–19, showing the anvil member of FIGS. 28 and 29 attached thereto.

FIG. 31 is a top view of a rotator member depicted in FIGS. 3 and 27.

FIG. 32 a side elevational view of the rotator member shown in FIG. 31.

FIG. 33 is a top view, on an enlarged scale, of a spacer element attached to the rotator member of FIGS. 31 and 32

FIG. 34 is a side elevational view of the spacer element of FIG. 33, from below in that drawing figure.

FIG. 35 is another side elevational view of the spacer element of FIG. 33, taken from above in that figure.

FIG. 36 is a rear elevational view of the spacer element of FIG. 33, taken from the right in that figure.

FIG. 37 is an exploded perspective view, showing the relationship among the anvil member of FIGS. 28–30, the rotator member of FIGS. 31 and 32, a staple release lever shown in FIG. 3, and a staple for plate shown in FIGS. 1 and 3.

FIGS. 38 and 39 are partial longitudinal cross-sectional views, on an enlarged scale, illustrating operation of a floating locking pin shown in FIG. 37.

FIG. 40 is a top view of the staple forming and timing plate of FIGS. 1, 3 and 37.

FIG. 41 is a top view, on an enlarged scale, of a cover plate shown in FIGS. 3 and 4.

FIG. 42 is a side elevational view of the cover plate of FIG. 41.

FIG. 43 is a side elevational view, on an enlarged scale, of the staple release lever shown in FIGS. 3 and 37.

FIG. 44 is atop view of the staple release lever of FIG. 43.

FIG. 45 is a partial longitudinal cross-sectional view showing the structural relationship among the staple release lever of FIGS. 43 and 44, the staple forming and timing plate of FIGS. 1, 3, 37 and 40, the channel member of FIGS. 16–19 and 30, the plastic body member of FIGS. 20–22 and the cover plate of FIGS. 3, 4, 41 and 42.

FIG. 46 is a top view, on an enlarged scale, of the staple cartridge of FIGS. 1–4, showing a first and a second cartridge body portion joined together.

FIG. 47 is a side elevational view of the first cartridge body portion of FIG. 46, showing a pair of staple holding springs and a stack of surgical staples.

FIG. 48 is a cross-sectional view taken along line 48—48 in FIG. 46.

FIG. 49 is a top view, on an enlarged scale, of the second cartridge body portion of FIG. 46.

FIG. 50 is an elevational view of the cartridge portion of FIG. 49, taken from below in that drawing figure.

FIG. 51 is an elevational view of the cartridge portion of FIG. 49, taken from above in that drawing figure.

FIG. 52 is a bottom view of the cartridge body portion of FIGS. 49–51.

FIG. 53 is a side elevational view, on an enlarged scale, of the first cartridge body portion of FIG. 46, taken from above in that figure.

FIG. 54 is a top view of the first cartridge body portion of FIG. 46, with the staple holding springs of that figure removed.

FIG. 55 is a side elevational view of the cartridge body portion of FIG. 54, taken from below in that figure.

FIG. 56 is an end elevational view of the cartridge body portion of FIG. 53, taken from the left in that figure.

FIG. 57 is an elevational view of a staple holding spring of FIGS. 46-48.

FIG. 58 is a side elevational view, on an enlarged scale, of a staple pusher shown in FIG. 47.

FIG. 59 is a top view of the staple pusher of FIG. 58.

FIG. 60 is an end elevational view of the staple pusher of FIGS. 47, 58 and 59, taken from the right in FIG. 58.

FIG. 61 is a side elevational view, on an enlarged scale, of a staple holding spring member shown in FIG. 47.

FIG. 62 is a top view of the staple holding spring of FIG. 61.

FIG. 63 is an elevational view, on an enlarged scale, of a surgical staple in accordance with the present invention.

FIG. 64 is a partial view of a distal end of the staple forming and timing plate of FIG. 40 in engagement with a surgical staple at the onset of a staple forming or bending operation.

FIG. 65 is a view similar to FIG. 64, showing a later stage during the staple bending operation.

FIG. 66 is a view similar to FIGS. 64 and 65, depicting the completion of the staple bending operation.

DETAILED DESCRIPTION

Figure 3:
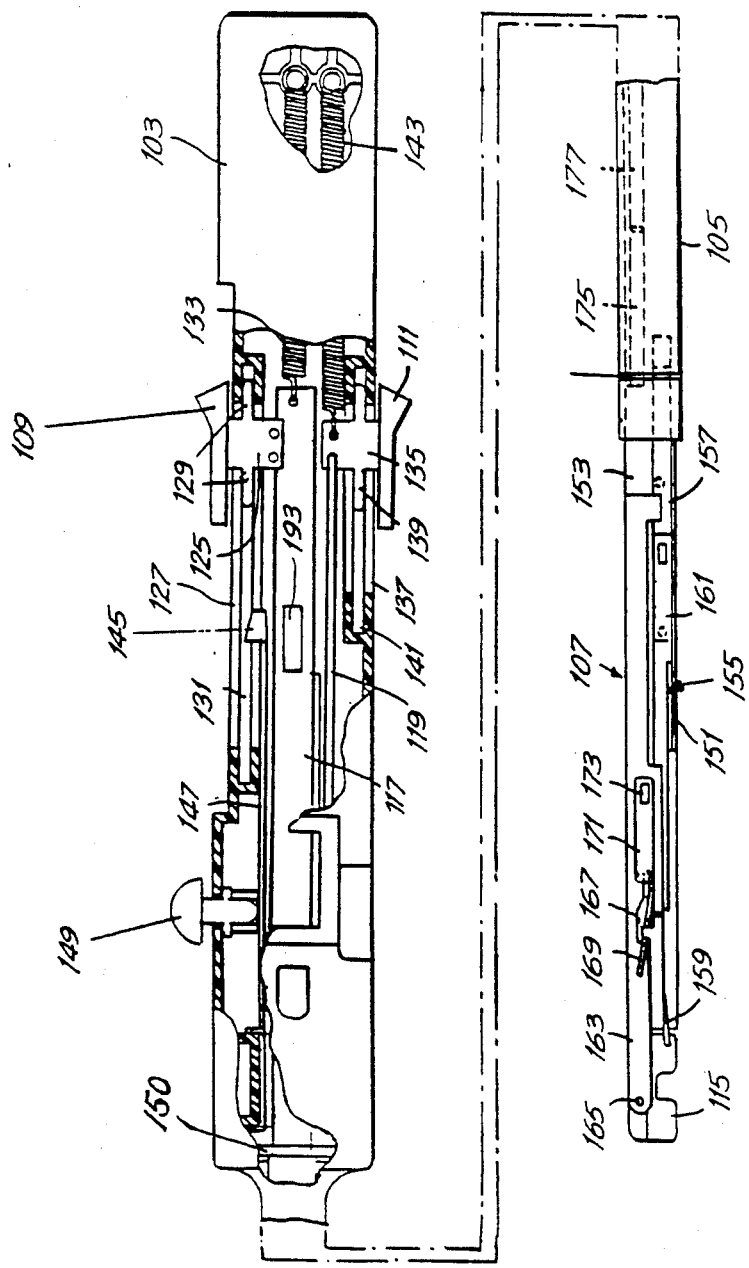
FIG. 3 is a side elevational view, on an enlarged scale, of the surgical instrument of FIGS. 1 and 2.

As illustrated in FIG. 1, a surgical instrument for suturing an opening such as a hernial tear in internal body tissues of a patient comprises an elongate frame 101 including a cylindrical handle portion 103, a handle extension 105 integral with handle portion 103, and a narrow superstructure assembly 107 inserted in and attached to handle portion 103 and extension 105. Handle portion 103 carries a first slidable button 109 for cocking the instrument, i.e., putting the instrument into a prefiring configuration, and a second slidable button 111 diametrically opposed to the first button for operating a tissue positioning assembly 113 shown in FIG. 2. First button 109 is mechanically coupled to a staple storing cartridge 115 via an elongate staple forming and timing plate 117 (FIG. 1), while second button 111 is operatively connected to tissue positioning assembly 113 via a gripper actuating rod 119 (FIG. 2). Handle portion 103 also carries an actuator lever 120 which is operatively linked to staple forming and timing plate 117 for shifting that element to bend a staple around an anvil as described in detail hereinafter.

FIG. 2 shows the prefiring configuration of the instrument, i.e., the configuration immediately prior to a pivoting of actuator lever 120. Button 109 is disposed in a forward position and staple storing cartridge 115 has been rotated from an aligned or longitudinal orientation shown in FIG. 1 to a transverse staple firing orientation. FIG. 2 illustrates in dashed lines a forward position of button 111 and a concomitant extended configuration of tong-like gripper members 121 and 123, the gripper members 121 and 123 being poised for gripping two pieces of body tissue on opposite sides of a hernial opening.

As depicted in FIG. 3, button 109 is formed with a planar projection 125 traversing a longitudinal and radial slot 127 in handle portion 103 and connected to a proximal end of staple forming and timing plate 117. Projection 125 is provided with one or two longitudinally extending arms 129 disposed in a longitudinal and circumferential slot 131 in handle portion 103 for bracing slidable button 109. The proximal end of staple forming and timing plate 117 is connected to handle portion 103 via a tension spring 133 which biases the plate element towards the proximal end of the instrument.

Button 111 is similarly formed with a planar projection 135 traversing a longitudinally elongate radial slot 137 in handle portion 103 and connected to a proximal end of actuator rod 119. Like projection 125 of button 109, projection 135 of button 111 is provided with one or two longitudinally extending arms or fins 139 disposed in a longitudinal and circumferential slot 141 in handle portion lOS for bracing slidable button 111. The proximal end of actuator rod 119 is connected to a tension spring 143 in turn connected to handle portion 103, whereby actuator rod 119 is biased towards the proximal end of the instrument. Plate element 117 and activator rod 119 pass through and are sealed within handle portion 103 by sealing disk 150.

Handle portion 103 is provided with a detent element 145 mounted the the handle via a leaf spring member 147. Detent 145 is engageable with a proximal edge of the rearward arm or fin 129 for preventing, upon the attainment of the prefiring configuration by the instrument, proximal motion of plate element 117 and concomitantly button 109 in response to the force exerted by tension spring 133. Detent 145 is disengageable from the rearward arm or fin 129 by manual pushing of a release button 149 slidably disposed in handle or housing 103.

Superstructure assembly 107 comprises two principal structural components: an elongate channel member 151, shown in detail in FIGS. 16-19, and a cooperating elongate plastic body member 153, shown in detail in FIGS. 20-22. Superstructure assembly 107 carries a rotator assembly 155 including a rotator member 157, which is engageable by staple forming and timing plate 117, and a rotator link 159 pivotably attached at a proximal end to rotator member 157 and at a distal end to a corner of staple cartridge 115. As explained in detail hereinafter with reference to FIGS. 37 and 67-72, the rotator assembly is responsive to a portion of the forward or distal motion of plate 117 to rotate cartridge 115 from an aligned or longitudinal orientation shown in FIG. 1 to a transverse staple firing orientation shown in FIG. 2. Rotator member 157 carries a slidably mounted rotator pin 343 (FIGS. 37 and 67-73) held against staple forming and timing plate 117 by a leaf spring 161.

Superstructure assembly 107 further comprises a cover plate 163 to a distal end of which the staple cartridge 115 is hingedly secured via a pivot pin 165. Cover plate 163 is provided with a cutout 167 through which a staple release lever 169 passes. As described hereinafter, staple release lever 169 is engageable with staple forming and timing plate 117 to control shifting of additional staples to cartridge 115 from a staple magazine (not shown in FIG. 3) in superstructure assembly 107. Staple release lever 169 is biased towards an open or staple release position by a leaf spring 171 attached by an ultrasonic weld at 173 to plastic body member 153.

Superstructure assembly 107 carries a slidably mounted staple pusher 175 which shifts additional staples longitudinally along superstructure assembly 107 towards cartridge 115. Staple pusher 175 is forced towards the distal end of the instrument by a compression spring 177.

Figure 4:
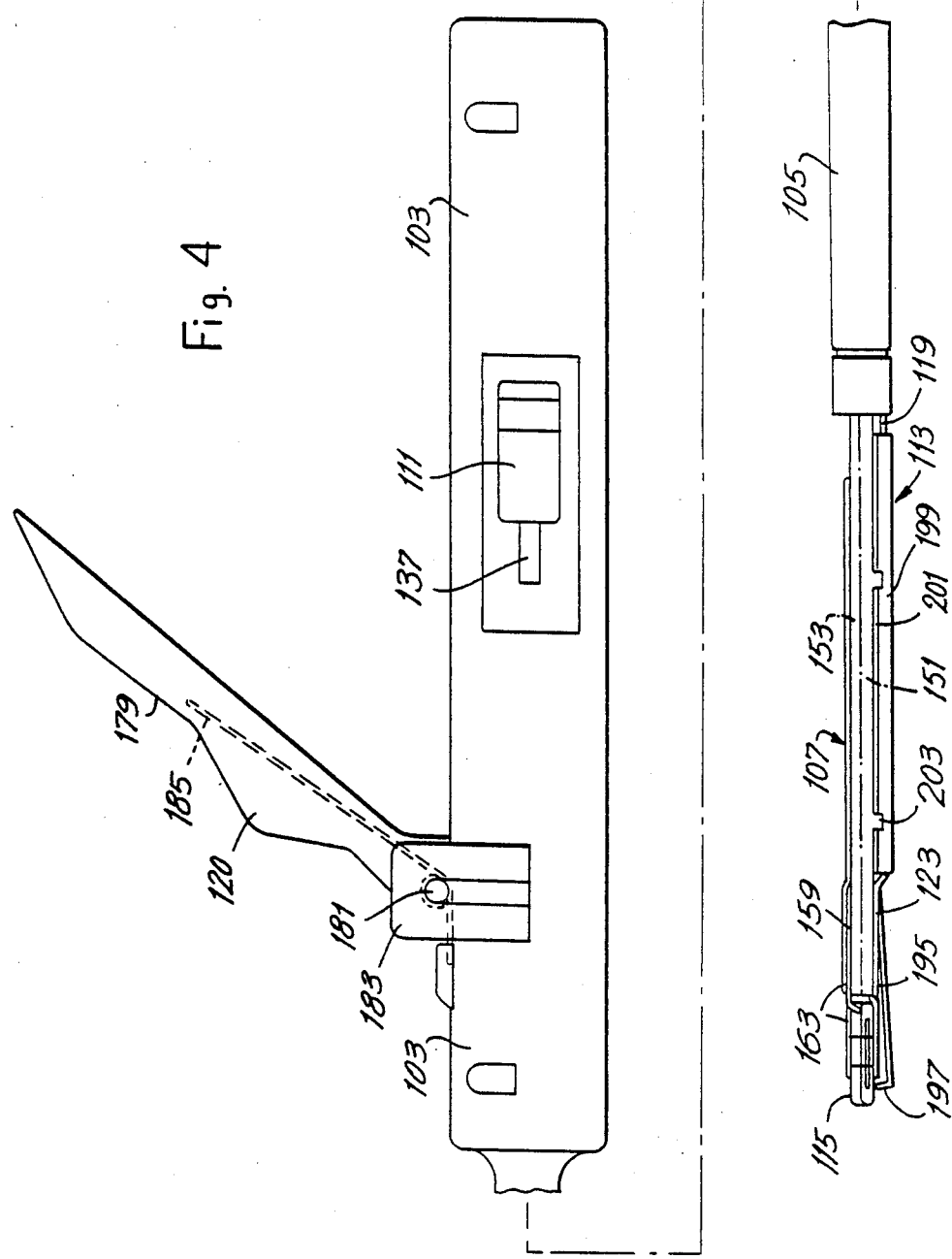
FIG. 4 is a view similar to FIG. 3, showing the surgical instrument rotated 90° about a longitudinal axis.
Figure 67:
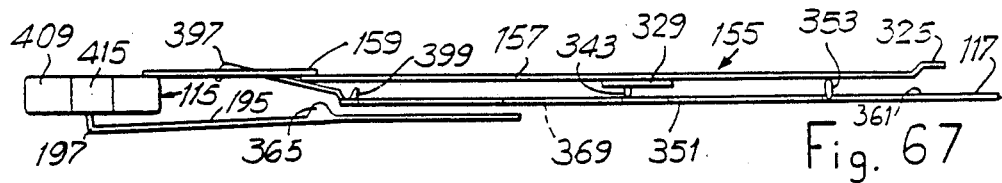
FIGS. 67-72 are diagrams illustrating successive steps in a cartridge rotation operation during which relative positions of selected components of a surgical instrument in accordance with the present invention change.

FIGS. 4 and 5 illustrate in side elevational view the actuator lever 120 of FIGS. 1 and 2. Actuator lever 120 has an outer profile line 179 designed to accommodate the fingers of a human hand and is hingedly secured via a pivot pin 181 to a pair of brackets 183 on handle portion 103. Actuator lever 120 is biased by a torsion spring 185 into an open or raised position shown in FIG. 4.

As illustrated in FIGS. 5 and 6, actuator lever 120 has a base portion 187 provided with a projecting lug 189 having a finger extension 191. Finger extension 191 traverses a slot 193 (FIG. 3) in staple forming and timing plate 117, whereby pivotal motion of actuator lever 120 causes a longitudinal motion of plate 117.

Additional components of superstructure assembly 107 illustrated in FIG. 4 include an elongate anvil member 195 having a proximal end attached to channel member 151 and a distal, free, end provided with a transversely extending anvil flange 197. As described hereinafter with reference to FIGS. 67-72, staple forming and timing plate 117 cooperates with anvil member 195 to shift anvil flange 197 in a transverse direction to prevent interference with the rotation of cartridge 115. FIG. 4 shows anvil member 195 in a shifted or bent configuration.

FIG. 4 also shows a tissue positioning assembly housing 199 fixed at a distal end to actuator rod 119 and having a pair of outwardly turned flanges 201 (only one visible in FIG. 4) slidably grasped by inwardly turned fingers 203 on channel member 151. The entire tissue positioning assembly 113 shifts longitudinally in response to motion of actuator rod 119.

Tissue Positioning Assembly

Tissue positioning assembly 113 is shown in greater detail in FIGS. 7-15. Tissue positioning assembly housing 199 takes the shape of a channel with flanges 201 disposed along an open side of the channel (FIG. 9). The housing has a base portion 205 with two different thicknesses at opposite ends. At a distal end, the base portion is provided on opposite longitudinally extending sides with a pair of elongate grooves 207 and 209 each terminating at a proximal end in a respective transversely extending groove 211 or 213. At a proximal end, base portion 205 of the tissue positioning assembly housing is similarly provided with an L-shaped groove 214 for receiving a hook-shaped distal end 215 (see FIG. 14) of actuator rod 119.

As depicted in FIGS. 7, 11 and 12, tong-like gripper members 121 and 123 are provided at their proximal ends with inwardly turned tips 217 and 219. Proximal portions of gripper members 121 and 123 are received in grooves 207 and 209 in housing base 205, inwardly turned tips 217 and 219 being seated in transverse grooves 211 and 213, respectively. Upon a disposition of gripper members 121 and 123 in grooves 207 and 209 and a placement of the hook-shaped distal end 215 of actuator rod 119 in L-shaped groove 214, a cover plate 221, shown in side elevation in FIG. 13, is fitted into channel-shaped housing 199 over the gripper members and the hook-shaped distal end of actuator rod 119.

Tong-like gripper members 121 and 123 are each formed at a central location with a respective bent portion 223 and 225, whereby a forward or distal end of each gripper member is staggered inwardly, i.e., towards the body of superstructure assembly 107 and cartridge 115 (see FIG. 4). The distal end portions of gripper members 121 and 123 take the form of outwardly bent fingers 227 and 229 having inwardly turned hooks 231 and 233. Fingers 227 and 229 of gripper members 121 and 123 are provided with respective collars 235 and 237 which serve as stops to limit the amount of tissue penetration by the fingers during a gripping operation and and which ensure that the tissue pieces are aligned in the same plane during an approximating and a subsequent stapling operation.

Channel or Housing Member

As shown in FIGS. 16-19, channel member 151 includes an elongate base 239 and two longitudinally extending side walls 241 and 243 (FIG. 18) attached thereto. The inwardly turned fingers 203 (FIG. 4) for slidably supporting tissue positioning assembly housing 199 each include a first segment 245 located in the same plane as a respective side wall 241 or 243 and a second segment 247 extending inwardly from the free end of the resepctive first segment, second segment 247 being disposed in a plane parallel to and spaced from the plane of channel base 239. The tissue positioning assembly support fingers 203 are formed by punching them out of base 239 and then bending them into an L-shaped configuration, channel base 239 being formed in the process with a plurality of apertures 249 in regions about support fingers 203.

A leading channel part in the form of a plate-shaped bracket 251 is connected to the distal end of channel member 151 via an inclined bight 253. Bracket 251 and bight 253 are provided with a rectangular opening 255 flanked on an outer side of channel member 151 by a pair of longitudinally and outwardly extending lugs 257. Rectangular opening 255 is traversed by tong-like gripper members 121 and 123, while lugs 257 serve as camming posts for inducing a closing of tong-like gripper members 121 and 123 during a retraction stroke thereof in response to the biasing force exerted by tension spring 143 (FIG. 3).

Bracket 251 is formed at a leading edge with a rectangular recess 259 traversed by anvil flange 197 in an operational position thereof. Bracket 251 is also formed at its leading edge with a hole 261 which receives a pivot pin (see pin 437 in FIGS. 53 and 55) for the mounting of cartridge 115.

To facilitate the attachment of channel member 151 to plastic body member 153, side walls 241 and 243 are provided with a plurality of upstanding lugs 263 which are bent over plastic body member 153 during assembly. Side wall 243 is additionally provided with a pair of upstanding T-shaped locking projections 265 which mate with similarly shaped indentations 267 along a side of plastic body member 153 (see FIGS. 20 and 22).

Plastic Body Member

Plastic body member 153 is depicted in detail in FIGS. 20–26. That member, like other non-load-bearing components of the surgical instrument, is preferably made of a synthetic resin material such as medical grade polycarbonate. FIGS. 23, 25 and 26 show that plastic body member 153 has a flattened generally T-shaped cross section which accommodates side walls 241 and 243 of channel member 151 (FIG. 25).

As illustrated particularly in FIGS. 20 and 23, plastic body member 153 is provided at a distal end with a longitudinally extending recess 269 which serves as a guide or track for rotator member 157. Recess 269 has a relatively narrow forward portion 271 and a widened rearward portion 273, a shoulder 275 being located at the junction between the forward portion and the rearward portion of recess 269. Shoulder 275 serves as an abutment which limits the displacement of rotator member 157 in the distal direction.

Forward portion 271 of recess 269 communicates with a longitudinally oriented groove 277 which receives a tip of rotator link 159, while rearward portion 273 of recess 269 is interrupted by an elongate essentially rectangular cutout 279 in plastic body member 153.

As shown in FIGS. 21 and 23–25, plastic body member 153 is provided along one side with an elongate longitudinal slot 281 which is closed by side wall 241 of channel member 151 (FIG. 25) to form a staple magazine for holding additional staples prior to their loading into cartridge 115. Staple pusher 175 (FIG. 3) extends at least partially into slot 281 for pushing staples therealong and into cartridge 115. At a distal end, plastic body member 153 has a cylindrical bore 283 which communicates with magazine slot 281. As described in greater detail below with respect to FIGS. 43–45, staple release lever 169 has at a front end a transversely extending segment 397 which passes through bore 283 and extends into magazine slot 281 for preventing a forward advance of staples under the action of compression spring 177 and staple pusher 175.

The distal end of plastic body member 153 is further provided with a prismatic recess 285 (see FIGS. 20 and 24) traversed by a semicylindrical hump 287. Hump 287 serves as a support point for staple release lever 169 (FIGS. 3 and 4). Distally of recess 285, a cylindrical lug 288 projects from an upper surface of plastic body member 153 for facilitating the attachment of cover plate 163 (FIG. 3) to plastic body member 153. Proximally of recess 285, a prismatic lug 289 projects from plastic body member 153 for enabling the attachment of leaf spring 171 to plastic body member 153. An upper surface of prismatic lug 289 is welded ultrasonically to leaf spring 171, as mentioned above.

One edge of plastic body member 153 is provided along a proximal half with a series of longitudinally spaced transversely oriented indentations 291 defined in part by respective ledges 293. Indentations 291 receive respective lugs 263 (FIGS. 18 and 19) of channel member 151, the lugs being bent during an assembly operation to conform to the shapes of the indentations. The same edge of plastic body member 153 is formed with T-shaped indentations 267 for receiving T-shaped locking projections 265 on channel member 151.

Along a longitudinally extending side of plastic body member 153 opposite indentations 267 and 291, member 153 is provided with a plurality of longitudinally spaced, rectangular recesses 295 in which lugs 263 on channel side wall 241 are disposed upon assembly of the instrument. On a proximal end portion of plastic body member 153 is attached a plate 297 which serves to secure compression spring 177 (FIG. 3).

FIG. 27 illustrates the distal end of superstructure assembly 107 with cover plate 163, anvil member 195 and bracket 251 removed. A rectangular space 299 is formed between base 239 of channel member 151 and a lower surface of plastic body member 153. That space houses staple forming and timing plate 117, as indicated in dot-dash lines in FIG. 25.

Anvil Member

Anvil member 195 (FIG. 4) is illustrated in detail in FIGS. 28 and 29. Anvil member 195 is basically an elongate metal strip having a narrow distal half 301 and a wider proximal half 303. Anvil flange 197 is disposed at the distal end of narrow strip half 301 which is further provided with a shallow bent U-shaped portion 302. Anvil member 195 carries at the distal end of wider strip half 303 a transversely extending semicircular camming projection 305. Projection 305 engages staple forming and timing plate 117 during a forward or distal motion thereof and thereby cooperates with that plate member to laterally bend anvil member 195 so that anvil flange 197 is removed, during a cartridge rotation operation, from engagement with cartridge 115 (see rest position of the anvil FIG. 3). As shown in FIG. 30, anvil member 197 is attached at a proximal end to channel member 151 via an ultrasonic or electrical spot weld 307. Camming projection 305 traverses a rectangular opening 309 in base 239 of channel member 151.

Rotator Assembly

The several components of rotator assembly 155 (FIG. 3) are shown in FIGS. 31–37. Rotator member 157 (FIGS. 31 and 32) is an elongate plate-shaped component having three contiguous portions 311, 313 and 315 of increasing width. The distal end of the most forward portion 311 is provided along one edge with a semicircular recess 317 which is traversed by a leg (not illustrated) of rotator link 159. That rotator link leg extends through recess 317 and into groove 277, as discussed hereinabove with reference to FIG. 20. The third, widest, portion 315 of rotator member 157 is provided at a forward end with a pair of circular apertures 319 and 321 and a rectangular aperture 323. A finger 325 is connected via an inclined web 327 to the rearward or proximal end of rotator member 157. The purpose and function of finger 325 and inclined web 327 are explained hereinafter with respect to FIG. 37–39.

As shown in FIG. 37, rotator assembly 155 includes a spacer element 329 attached to a side of rotator member 157 facing staple forming and timing plate 117. The spacer element is depicted in detail in FIGS. 33–36. Spacer element 329 has an elongate prismatic body 331 with a pair of elongate flanges 333 and 335 in the form of cross-sectionally rectangular beads extending the length of spacer body 331. At a distal end, spacer body 331 is formed with a transverse cylindrical post or peg 337 and a circular hole 339, while at a proximal end, the spacer body has an upstanding prismatic post or peg 341. Cylindrical peg 337 mates with circular aperture 319 in rotator member 157 (FIG. 31), while prismatic peg 341 traverses rectangular aperture 323. To a free end of peg 341 leaf spring 161 (FIG. 3) is ultrasonically or electrically welded.

Rotator assembly 155 further includes a pin 343 (FIG. 37) which is slidably inserted through hole 339 of spacer element 329 and aperture 321 of rotator member 157. Pin 343 has a pointed or conical free end 345 which coacts with beveled ends 347 and 349 of a slot 351 in staple forming and timing plate 117 (FIGS. 37 and 40) to properly control and time the operation of rotator assembly 155. Prior to the commencement of a cartridge rotating operation, conical end 345 of pin 343 engages a surface of staple forming and timing plate 117, as indicated generally in the exploded view of FIG. 37, while the upper end of the pin projects through aperture 321 to slightly bend leaf spring 161 on an opposite side of rotator member 157.

Upon a forward motion of plate 117 pin 343 drops into slot 351 under the force exerted by spring 161, and conical pin end 345 contacts the beveled proximal end 349 of slot 351. The angles of inclination of conical end 345 and beveled end 349 and the associated coefficients of friction are such that rotator member 157 is entrained during continued forward motion of staple forming and timing plate 117. At the termination of a rotation operation, the distal end of spacer element 329 contacts shoulder 275 of plastic body member 153 (FIG. 20) and thereby stops the forward motion of rotator member 157. Upon the arrest of rotator member 157, pin 343 slides upwardly along beveled slot end 349 and is thus transversely displaced in opposition to the force exerted by leaf spring 161 so that, during further forward motion of staple forming and timing plate 117, conical pin end 345 slidingly engages a major planar surface of the staple forming and timing plate.

As illustrated in FIGS. 37, 38 and 39, rotator assembly 155 further includes a floating pin 353 slidably disposed in a transverse bore 355 in plastic body member 153. Floating pin 353 has a conical first end 357 and a conical second end 359. Prior to the termination of a rotation operation by rotator assembly 155, conical end 357 of floating pin 353 traverses or is disposed in a slot 361 in staple forming and timing plate 117 (FIGS. 37-40). Upon an arrest of forward motion of the staple forming and timing plate by the contact between spacer element 329 and shoulder 275, conical pin end 357 cams against a beveled end 363 of slot 361, whereby pin 353 is transversely displaced in bore 355 so that, during further forward motion of staple forming and timing plate 117, conical pin end 359 is disposed in the plane of rotator member 157 and contacts inclined web 327 (FIG. 32) to lock rotator member 157 against rearward motion during a stapling operation. Finger 327 serves to prevent floating pin 353 from leaving slot 355.

As depicted in FIG. 40, staple forming and timing plate 117 has a distal end formed with a pair of longitudinally extending prongs 365 which define a rectangular recess 367. As described in detail hereinafter with reference to FIGS. 64–66, prongs 365 cooperate with anvil flange 197 to deform a surgical staple from an open configuration to a closed configuration. Staple forming and timing plate 117 is also provided at a distal end with a longitudinally extending slot 369 which enables the disposition of anvil flange 197 in the stapling plane upon the completion of a cartridge rotation operation. Two additional slots 371 and 373 in staple forming and timing plate 117 respectively serve to limit the motion of the staple forming and timing plate in both the distal and proximal directions and to receive finger extension 191 of actuator lever 120 so that the lever can move staple forming and timing plate 117 in the distal direction during a power stroke of a stapling operation.

Cover Plate

FIGS. 41 and 42 show in detail the structure of cover plate 163 (see FIGS. 3 and 4). The distal end of the cover plate is formed with a circular hole 375 receiving cartridge pin 165 (FIGS. 3 and 53–55), an aperture 377 for receiving cylindrical lug 288 (FIGS. 20–22), and another aperture 379 which is aligned with bore 283 for receiving a distal part of staple release lever 169. The distal end of cover plate 163 is further provided with a rectangular recess 381 for receiving a lug 263 on channel member side wall 241 upon a bending of the lug during assembly of the surgical instrument. A linear cut 378 extends longitudinally from the end of cover plate 163 to cutout 167, thereby separating the distal end of the cover plate into two parallel sections 383 and 385. Section 385 is bent to occupy a plane transversely staggered with respect to the plane of the other section 383 and the body of cover plate 163 (see FIG. 42). Cover plate 163 also has a rectangular opening 387 through which prismatic lug 289 of plastic body member 153 (see FIGS. 20–22) projects, while one side edge of cover plate 163 is formed at a proximal end with a large rectangular cutout 389 coextensive with cutout 279 on plastic body member 153.

As shown in FIG. 43, section 385 of cover plate 163 is provided with a laterally extending rectangular lug 386 which overlies staple release lever 169 and serves to hold that lever in position. The relationship between lug 386, staple release lever 169 and hump 287 of plastic body member 153 (see FIGS. 20 and 24) is depicted in FIG. 43. Lug 386 and hump 287 are disposed on opposite sides of the staple release lever and cofunction to limit the transverse displacement of and to form a fulcrum point for that member.

Staple Release Lever

Staple release lever 169 has two straight coplanar body segments 391 and 393 inclined with respect to one another and interconnected by a bight segment 395. At a distal end, body segment 391 is provided with a transversely extending leading segment 397 which passes through aperture 379 in cover plate 163 (FIG. 41) and bore 283 in plastic body member 153 (FIGS. 20 and 23), as pointed out above. At a proximal end, body segment 393 is integral with a U-shaped camming segment 399 which is bent slightly out of the plane of body segments 391 and 393 (FIG. 44).

As illustrated in FIG. 45, U-shaped camming segment 399 of staple release lever 169 is disposed in a prismatic recess 401 in plastic body member 153 (FIG. 20) and engages a surface of staple forming and timing plate 117 essentially during all motion thereof. However, prior to an initial forward motion of the staple forming and timing plate, i.e., prior to the cocking of the instrument by button 109 (FIGS. 1–3), U-shaped camming segment 399 extends into the rectangular space 299 defined by channel member 151 and plastic body member 153. In that neutral configuration of the instrument, leading segment 397 of staple release lever 169 does not traverse any part of magazine slot 281. Upon a pivoting of staple release lever 169 about hump 287 during an initial forward motion of staple forming and timing plate 117, leading segment 397 of the staple release lever enters magazine slot 281 to prevent passage of staples therealong.

The staple forming and timing plate moves forward, i.e., towards the distal end of the instrument, initially in response to the cocking movement of button 109 (see FIGS. 1-3). Upon the attainment by the instrument of a prefiring configuration and upon the manipulation of button 111 to grip new portions of internal body tissues, actuator lever 120 is then pivoted to provide a power stroke of staple forming and timing plate 117.

Staple Cartridge

As illustrated in FIG. 46, 47 and 48, staple cartridge 115 comprises a first body portion 403 and a second body portion 405 attached to one another by ultrasonic or electrical spot welding along a joint 407. First body portion 403, shown by itself in FIGS. 49-52, is generally U-shaped and has a pair of arms 409 and 411 connected by a bight portion 413. Arms 409 and 411 and bight portion 413 define a prismatic recess 415 in which anvil flange 197 is disposed during a stapling operation. Body portion 403 is further formed with an elongate slot 417 having a flattened T shape and extending through both arms 409 and 411, as well as bight portion 413. During deformation of a surgical staple into a closed configuration, staple forming and timing plate 117 passes through the central, wider portion of slot 417 and the bending of the staple around anvil flange 197 takes place at least partially in slot 417. Arms 409 and 411 accordingly extend from bight portion 413 to prevent a twisting of the staple during a staple forming operation prior to entry of the staple into the tissue.

On a side opposite arms 409 and 411, first body portion 403 of cartridge 115 is provided with a flat projection 419 which is inserted into second body portion 405 (see FIG. 48). First body portion 403 is additionally provided with a pair of grooves 421 and 423 which communicate with respective holes 425 and 427 in the body portion. The grooves and the holes receive portions of respective staple holding springs 429 and 431, illustrated in FIGS. 46-48. In addition, arm 411 of the first body portion 403 is formed in one corner with a cylindrical bore 433 which receives an end of rotator link 159 (FIGS. 3 and 4).

FIGS. 53-56 show in detail the structure of body portion 405 of cartridge 115. Body portion 405 takes basically an elongate prismatic shape provided on opposite sides with a pair of outwardly extending cylindrical lugs or pegs 165 and 437. As mentioned hereinabove, peg 165 is received in hole 375 of cover plate 163, while peg 437 is received in hole 261 on bracket 251 of channel member 151. Body portion 405 is also provided on opposite sides with two pairs of grooves 439, 441 and 443, 445 in which staple holding springs 429 and 431 are seated.

Cartridge body portion 405 defines a staple storing chamber 447 which communicates with an elongate passageway 449 through which staple forming and timing plate 117 moves during a stapling operation. One corner of body portion 405 is cut out to form a rectangular recess 451 which communicates with chamber 447 via a staple entrance gap 453 defined in part by two beveled surfaces 455 and 457.

As depicted in FIGS. 47 and 48, staple holding springs 429 and 431 substantially surround cartridge body portion 405 and have portions extending transversely through cartridge 115 and across slot 417 to hold surgical staples 459 in cartridge 115. The portions of springs 429 and 431 which extend into slot 417 are bent outwardly, under force transmitted via staple forming and timing plate 117, to allow passage of a staple during a stapling operation. Staple holding spring 431 alone is illustrated in FIG. 57.

As indicated in FIG. 47, cartridge 115 also carries a staple pusher 461 and a staple biasing spring 463. Staple pusher, shown in detail in FIGS. 58-60, essentially takes the form of a flat plate 465 provided along two edges with a rim 467 and having an angled flange or wing 469 extending from another edge. Along an edge or long side of plate 465, rim 467 is formed with a rectangular recess 471, plate 465 having a rectangular finger 473 disposed next to the recess and in the plane of the plate. Finger 473 projects into an opening or window 474 (FIG. 53) provided on a rear wall of cartridge body portion 405 to limit the range of motion of staple pusher 461 within chamber 447 (FIG. 55).

FIGS. 61 and 62 illustrate staple biasing spring 463 in detail. The spring includes a central body 475 having two winglike extensions 477 and 479 projecting at an angle with respect to body 475. The body additionally has a neck or head projection 481 which, like finger 473 of staple pusher 461, passes through opening or window 474.

Staple and Staple Bending Operation

A staple 459 used in a surgical instrument pursuant to the present invention comprises a pair of legs 483 and 485 connected to one another via a bight section 487, as shown in FIG. 63. Each leg 483 and 485 is oriented preferably at an acute angle $B_1$ of approximately 80° to 85° with respect to bight section 487. In addition, the free end of each leg 483 and 485 is chamfered at an angle $B_2$ of approximately 60° with respect to bight section 487. The inclination of the staple legs serves in part to prevent the legs from bending and to prevent the tissue from slipping off of the legs during a staple closing operation.

At the onset of a staple bending or deformation process, depicted in FIGS. 64-66, prongs 365 of staple forming and timing plate 117 engage bight section 487 at opposite ends thereof and push the bight section against anvil flange 197. As staple forming and timing plate 117 continues its forward or distal motion in response to a power stroke of actuator lever 120, bight section 487 bends inwardly at the edges of anvil 197 (FIG. 65). At the termination of the power stroke of actuator lever 120 and staple forming and timing plate 117, staple 459 has assumed a generally rectangular shape (FIG. 66) with the free ends of staple legs 483 and 485 overlapping one another in a criss-cross configuration. The inclination of the staple legs with respect to the bight portion and the concomitant criss-cross configuration of the staple legs in the bent state of the staple serves to tightly lock the tissue pieces to one another. It is to be noted that anvil flange 197 has a width which is less than the width of rectangular recess 367 so that prongs 365 can bend staple 459 around anvil flange 197 as shown in the drawing figures.

Cartridge Rotation Operation

Figure 71:
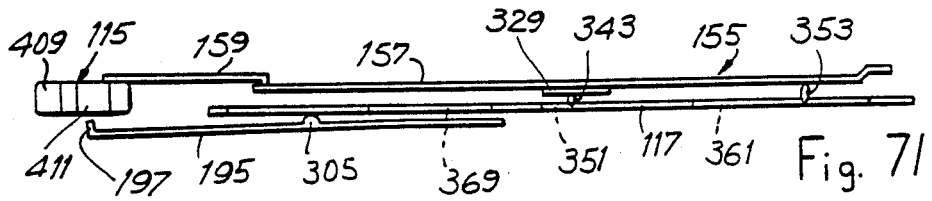
Figure 72:
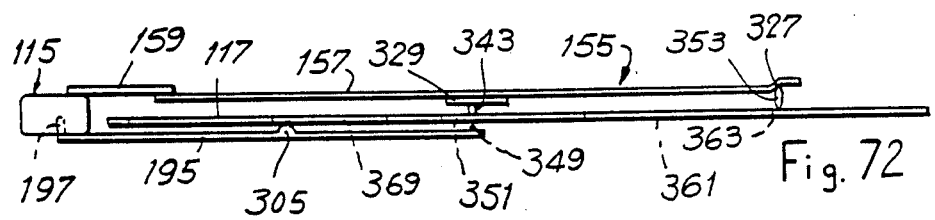
Figure 73:
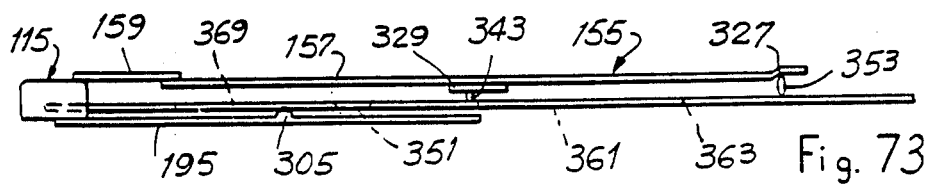
FIG. 73 is a diagram similar to FIGS. 67-72, showing the relative positions of the components of those drawing figures at the termination of the staple bending operation, shown in FIG. 66.

FIGS. 67 through 72 depict successive steps in the rotation of cartridge 115 by rotator assembly 155, while FIG. 73 shows a final stage in a staple bending operation. In a neutral or precocking configuration of the surgical instrument, shown in FIG. 67, anvil flange 197 rests against an outer surface of cartridge 115. In addition, staple release lever 169 is in an angled or opened orientation in which the leading segment 397 of the staple release lever is removed from the staple path along magazine slot 281 (FIGS. 20–21, 23–25 and 45). In this orientation of staple release lever 169, staples 459 can be shifted by staple pusher 175 and compression spring 177 (FIG. 3) from magazine slot 281 through staple entrance gap 453 (FIG. 56) into staple holding chamber 447 (FIG. 55) of cartridge 115. Provided that the staple holding chamber is not already filled with surgical staples 459, an additional staple entering the cartridge through gap 453 slides against flange or wing 469 of pusher 461 and into the cartridge.

In the neutral or precocking configuration of the instrument, U-shaped camming segment 399 of staple release lever 169 is partially disposed in recess 367 at the distal end of staple forming and timing plate 117 (alternatively, segment 399 may be disposed distally of a prong 365 of plate 117). Under pressure exerted by leaf spring 161 (FIG. 3), rotator pin 343 engages a major surface or face of staple forming and timing plate 117 proximally of slot 369, while floating pin 353 projects downwardly into slot 361 (see also FIG. 38).

Figure 68:
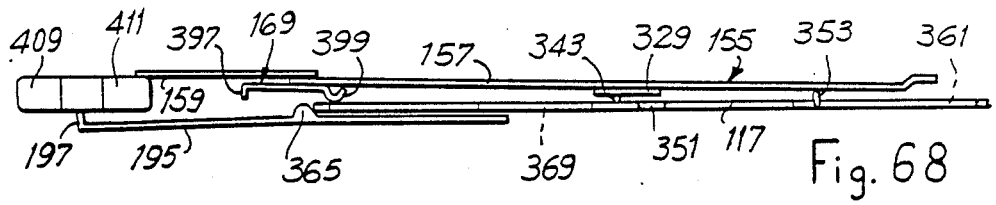

Upon the initiation of a cartridge rotation operation, staple release lever 169 is pivoted about hump 287 (FIGS. 20 and 24) by the engagement of U-shaped camming segment 399 with a leading end of staple forming and timing plate 117. As illustrated in FIG. 68, staple release lever 169 is rotated into a staple holding orientation generally parallel to staple forming and timing plate 117. In this orientation of the staple release lever, leading segment 397 thereof extends at least partially into magazine slot 281 and locks the staples therein against shifting towards cartridge 115 (see FIG. 45). Inasmuch as staple release lever 169 maintains the same staple holding orientation throughout the remainder of the cartridge rotation cycle, the staple release lever has been omitted from FIGS. 69–73.

Figure 69:
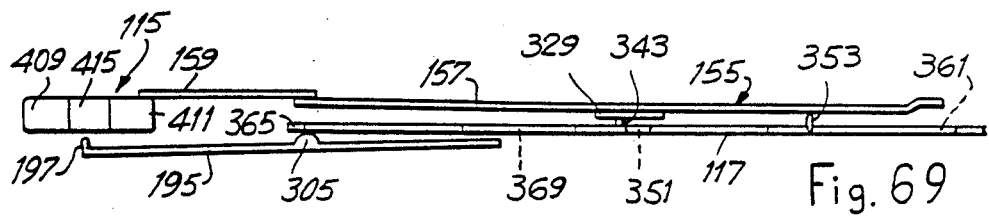

Upon further forward motion of staple forming and timing plate 117 during a cocking of the instrument via pushbutton 109 (FIGS. 1–3), camming projection 305 on anvil member 197 contacts a prong 365 of plate 117 and, in camming against that plate, further bends the anvil member and concomitantly shifts anvil flange 197 from cartridge 115, as indicated in FIG. 69.

Figure 70:
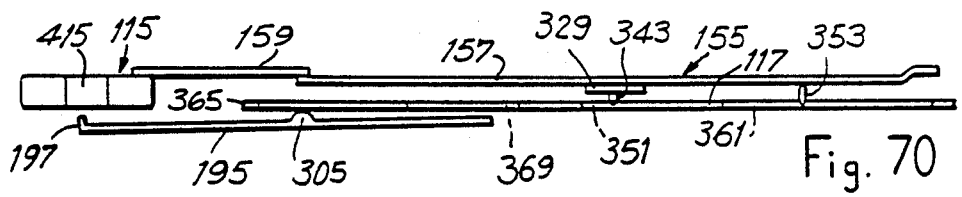

After the lateral shifting of anvil flange 197 and upon further forward motion of staple forming and timing plate 117, rotator pin 343 drops into slot 351 on staple forming and timing plate 117 under pressure exerted on the pin by leaf spring 161. The conical free end 345 of pin 343 then contacts the beveled proximal end 349 of slot 351 (FIG. 70). As stated above, the angles of inclination of conical end 345 and beveled end 349 and the associated coefficients of friction are such that rotator member 157 is entrained by staple forming and timing plate 117. Upon engagement of conical pin end 345 and beveled slot end 349, forward motion of the staple forming and timing plate pushes rotator member 157 and rotator link 159 towards the distal end of the instrument. That longitudinal motion causes a rotation of cartridge 115, as indicated in FIGS. 70–72.

Upon a 90° rotation of cartridge 115, the distal end of spacer element 329 abuts against shoulder 275 (FIG. 20) and thereby prevents further forward motion of rotator member 157. Further forward motion of staple forming and timing plate 117 during the cocking operation causes pin 343 to cammingly slide along beveled end 349 of slot 351 and thereby shift in a transverse direction in opposition to the biasing force exerted by leaf spring 161. Pin 343 then once again contacts a major longitudinal surface of the staple forming and timing plate (FIGS. 72 and 73). At the same time, floating pin 353 ascends beveled end 363 of slot 361 and engages inclined web 327 to lock rotator member 157 against rearward or proximal motion. Subsequently, camming projection 305 on anvil member 195 enters slot 369 in staple forming and timing plate 117. Upon the termination of a cocking operation executed via pushbutton 109 (FIG. 1–3), the various operative components of the surgical instrument have the prefiring configuration illustrated in FIG. 72.

During the power stroke of actuator lever 120 and staple forming and timing plate 117, camming projection 305 is disposed within slot 369 of the staple forming and timing plate, while the rotator assembly 155 remains looked into position by the coaction of spacer element 329 and shoulder 275, on the one hand and floating pin 353 and inclined web 327 on the other hand. The power stroke of the device deforms a staple 459 into a closed configuration, as discussed hereinabove with reference to FIGS. 64–66.

Use in Corrective Surgery

Figure 74:
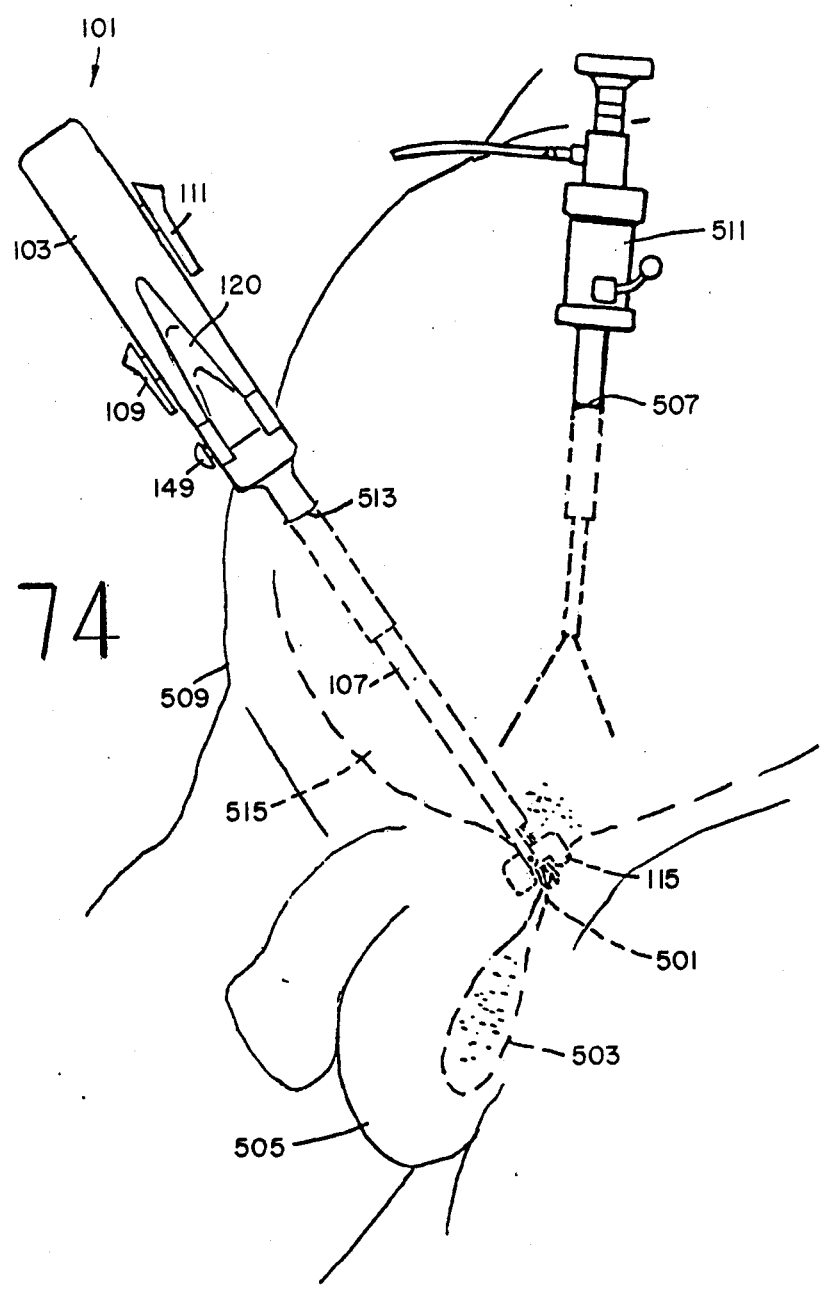
FIG. 74 is a schematic perspective view of a patient with a hernial tear in a region about the patient's scrotum, showing use of the instrument in accordance with the present invention.

FIG. 74 illustrates a stage in a surgical procedure using an instrument 101 in accordance with the present invention. As indicated in the drawing, a hernial opening 501 in the abdominal wall of a patient may lead to a sac 503 which may contain intestinal material. Both the sac and the intestinal material contained therein may lie in the scrotal sac 505.

A surgeon (not shown) first makes a small incision 507 at a point on a patient's body 509 remote from the hernial opening 501 deep within the body wall of the patient. A laproscope 511 is inserted through the incision and guided inwardly until the area of the hernia is visible to the surgeon. A second small incision 513 approximately one-half inch in length is made through the external body wall of the patient at another site on the patient's body remote from the hernial tear 501.

A distal portion of instrument 101, with the staple cartridge 115 aligned with the superstructure 107, is inserted through the incision 513 and advanced through the body cavity 515 so that a distal end of the instrument lies close to the hernial opening 501 while remaining on the internal side of the opening. As described hereinabove with reference to FIGS. 67–72, button 109 is then pushed in a distal direction to rotate cartridge 115 and to put the instrument 101 in a prefiring configuration. Subsequently, button 111 is pushed forwardly to open tong-like gripper members 121 and 123 and to shift them in the distal direction. The instrument is then manipulated until the inwardly turned hooks 231 and 233 have been inserted into respective pieces of internal body tissue on opposite sides of hernial tear 501 at points near an end of the hernial opening. Button 111 is released and tension spring 143 (FIG. 3) pulls gripper members 121 and 123 rearwardly so that the two pieces of body tissue on opposite sides of the hernail opening 501 are gripped, approximated and held together by tissue positioning assembly 113. It is to be noted at this juncture that the tissue gripping, approximating and holding is accomplished from the internal side of the hernial opening.

Upon the retraction and closing of tong-like gripper members 121 and 123 through the action of tension spring 143, the two pieces of body tissue are stapled together from the internal side of the opening, the step of stapling being performed by squeezing actuator lever 120 against handle portion 103 of the instrument. The staple 459 is then bent into a closed configuration holding the two pieces of tissue together, as discussed hereinabove.

Upon the execution of the first suture, tissue positioning assembly 113 is operated to release the gripped tissues and cartridge 115 is rotated back into a longitudinal orientation in which the cartridge is aligned with superstructure assembly 107. This counterrotation enables the loading of another staple into cartridge 115 and the removal of the formed staple suture from the anvil flange 197. Cartridge 115 is then rotated again as described hereinabove with respect to FIGS. 67–72, whereupon the instrument is again manipulated to insert hooks 231 and 233 into the respective pieces of internal body tissue on opposite sides of hernial tear 501 at points proximate to but spaced from the suture. As before, button 111 is released and tension spring 143 (FIG. 3) pulls gripper members 121 and 123 rearwardly so that the two pieces of body tissue on opposite sides of the hernail opening 501 are gripped, approximated and held together by tissue positioning assembly 113. The operation proceeds in this manner until the hernial opening or tear 501 is closed. Subsequently, the staple cartridge is rotated into its longitudinal or aligned orientation prior to removal of instrument 101 from the patient's body 509.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A surgical instrument for suturing an opening in internal body tissues of a patient from inside the body cavity of the patient, said instrument comprising:
    elongate frame means for providing a superstructure for the instrument;
    staple storing means on said frame means for temporarily storing at least one staple;
    staple forming and ejection means at least in part movably mounted to said frame means for ejecting said staple from said stable storing means into the body tissues of the patient and deforming said staple from an open position to a closed position in which said staple holds together two pieces of body tissue on opposite sides of said opening;
    first actuating means at least in part movably mounted to said frame means and connected to said staple forming and ejection means for moving at least a portion thereof;
    tissue positioning means separate from said staple forming and ejection means and mounted to said frame means for gripping, approximating and temporarily holding in a stapling position said two pieces of body tissue prior to and during a stapling operation; and
    second actuating means separate from said first actuating means for moving at least a portion of said tissue positioning means prior to said stapling operation, said second actuating means being at least in part movably mounted to said frame means and connected to said tissue positioning means.

2. The instrument defined in claim 1 wherein said tissue positioning means includes a pair of tong-like gripper members mounted to said frame means for longitudinal motion therealong and camming means for changing a distance between said tong-like gripper members during motion thereof so that during a closing stroke said tissue positioning means simultaneously draws said two pieces of body tissue together and towards said staple storing means.

3. The instrument defined in claim 2 wherein said second actuating means includes an actuator member mechanically connected to said tong-like gripper members and further includes biasing means engaging said actuator member for biasing said tong-like gripper members towards a closed configuration.

4. The instrument defined in claim 3 wherein said biasing means includes a tension spring fastened at one end to said frame means and at an opposite end to said actuator member.

5. The instrument defined in claim 4 wherein said second actuating means includes a knob for enabling an operator to push said actuator member from a proximal end of the instrument towards a distal end thereof in opposition to a force exerted by said tension spring.

6. The instrument defined in claim 2 wherein each of said tong-like gripper members is provided with means including a collar-like element for limiting the amount of insertion of said tong-like gripper members into the body tissues of the patient.

7. The surgical instrument of claim 1 further comprising a plastic body member which has at an end a longitudinally extending recess which serves as a guide for said rotating means.

8. The instrument defined in claim 1 wherein said instrument includes a distal end adjacent which at least part of said staple forming and ejection means and at least of part said tissue positioning means are exposed from said frame means, said instrument also including a proximal end and means mounted to said frame means for sealing fluid-tight said distal end of said instrument from said proximal end of said instrument.

9. A surgical instrument for suturing internal body tissues of a patient reached through a relatively small incision, comprising:
    an elongate relatively narrow frame suitable to be passed through said relatively small incision;
    a staple cartridge mounted to said elongate frame;
    means for moving said stable cartridge from a first orientation aligned with said frame and not substantially increasing the profile of said frame to a second orientation transverse to said frame for staple ejection, whereby said frame may be passed through said relatively small incision when said cartridge is in said first orientation aligned with said frame means and then said cartridge may be moved to said second orientation transverse to said frame for staple ejection; and
    means for ejecting a staple into the internal body tissues of said patient and for closing said staple.

10. The surgical instrument defined in claim 9 wherein said means for ejecting a staple comprises a staple forming plate movably mounted to said elongate frame for ejecting a staple from said cartridge and deforming said staple from an open position to a closed position in which said staple holds together two pieces of body tissue on opposite internal sides of said hernial opening.

11. The surgical instrument defined in claim 9 further comprising a means for tissue positioning, said means for tissue positioning mounted on said elongate frame separate from said staple ejection means and functioning to grip, approximate and temporarily hold together two pieces of body tissue prior to and during a stapling operation.

12. The surgical instrument defined in claim 9 wherein said means for tissue positioning comprises a pair of tong-like gripper members mounted to said elongate frame for longitudinal motion therealong, and a camming element for changing the distance between the tong-like gripper members during motion thereof so that during a closing stroke the means for tissue positioning draws two pieces of body tissue together and towards the staple cartridge.

13. The surgical instrument defined in claim 9 wherein said means for moving said staple cartridge comprises a rotator member slidably mounted to said elongate frame for longitudinal motion therealong, a link pivotably attached at one end to said staple cartridge and at an opposite end to said rotator member, and a timing mechanism mounted to said elongate frame for controlling the initiation and duration of motion of the rotator member.

14. The surgical instrument defined in claim 13 wherein said timing mechanism comprises a slot in an elongate plate element movably mounted to said elongate frame and a pin on said rotator member coating with the slot.

15. The surgical instrument defined in claim 13 wherein said means for moving further comprises a biasing spring for forcing against said elongate plate element, and a plurality of coacting stop members provided on said rotator member and said elongated frame for limiting the range of longitudinal motion of said rotator member and concomitantly the range of rotational motion of the cartridge.

16. The surgical instrument defined in claim 9 wherein said staple cartridge comprises a staple chamber having an inlet opening, a biasing spring and a staple plate mounted therein, said biasing spring and plate functioning to enable the reception and storage of additional staples by the cartridge subsequently to the stapling operation, and a plurality of spring tines for preventing a staple from falling out of said stable chamber prior to a staple ejection operation.

17. A surgical instrument for suturing an opening in internal body tissues of a patient from inside the body cavity of the patient, said instrument comprising:
 elongate frame means for providing a superstructure for the instrument;
 staple storing means on said frame means for temporarily storing at least one staple, said staple storing means including an elongate staple cartridge rotatably mounted to said frame means at a distal end thereof, and further comprising rotator means operatively connected to said cartridge for rotating said cartridge from an orientation aligned with said frame means to a staple ejection orientation transverse to said frame means;
 staple forming and ejection means at least in part movably mounted to said frame means for ejecting said staple from said stable storing means into said body tissues and deforming said staple from an open position to a closed position in which said staple holds together two pieces of body tissue on opposite sides of said opening;
 first actuating means at least in part movably mounted to said frame means and connected to said staple forming and ejection means for moving at least a portion thereof;
 tissue positioning means separate from said staple forming and ejection means and mounted to said frame means for gripping, approximating and temporarily holding in a stapling position said two pieces of body tissue prior to and during a stapling operation;
 second actuating means separate from said first actuating means for moving at least a portion of said tissue positioning means prior to said stapling operation, said second actuating means being at least in part movably mounted to said frame means and connected to said tissue positioning means.

18. The instrument defined in claim 17 wherein said cartridge includes a staple chamber and means including spring tines for preventing a staple from falling out of said chamber prior to a staple ejection operation.

19. The instrument defined in claim 18 wherein said cartridge is provided with means for receiving and storing additional staples subsequently to said stapling operation, said means for receiving and storing including an inlet opening, a biasing spring and a staple plate.

20. The instrument defined in claim 17 wherein said rotator means includes a rotator member slidably mounted to said frame means for longitudinal motion therealong and a rotator link pivotably attached at one end to said cartridge and at an opposite end to said rotator member.

21. The instrument defined in claim 20, further comprising timing means mounted to said frame means for controlling the initation and duration of motion of said rotator member.

22. The instrument defined in claim 2 wherein said staple forming and ejection means includes an elongate plate element movably mounted to said frame means, said timing means including a slot formed in said elongate plate element and a pin on said rotator member coacting with said slot.

23. The instrument defined in claim 2 wherein said rotator means further includes spring biasing means for forcing said pin against said elongate plate element.

24. The instrument defined in claim 23, further comprising stop means including coacting elements on said rotator member and said frame means for limiting a range of longitudinal motion of said rotator member and concomitantly limiting a range of rotational motion of said cartridge.

25. The instrument defined in claim 24, wherein said slot is provided with beveled ends and said pin is formed with a substantially conically shaped free end, whereby said pin is compelled to moved transversely out of said slot upon an arresting of longitudinal motion of said rotator member by said stop means.

26. The instrument defined in claim 5 wherein said stop means includes a floating pin slidably mounted to said frame means for controlled movement in a direction transverse thereto, a shoulder at a proximal end of said rotator member and an additional slot in said elongate plate element, said additional slot being formed with a beveled proximal end and said floating pin being provided with conically shaped ends, whereby said floating pin is forced in a camming type motion transversely out of said slot upon an engagement of said floating pin with said beveled proximal end during relative motion of said elongate plate element and said rotator member after termination of a cartridge rotation operation and is simultaneously moved into a locking engagement with said shoulder.

27. The instrument defined in claim 2 wherein said staple forming and ejection means includes an anvil member with an anvil flange projecting, during said stapling operation, into a staple forming plane intersecting said cartridge, further comprising shifting means for moving said anvil flange transversely away from said staple forming plane prior to a cartridge rotation operation.

28. The instrument defined in claim 27 wherein said staple forming and ejection means includes an elongate plate element movably mounted to said frame means, said timing means including a slot formed in said elongate plate element and a pin on said rotator member coacting with said slot, said anvil member being an elongate member with a proximal end attached to said frame means and a distal end carrying said anvil flange, said shifting means including a camming projection on said anvil member engageable with said plate member.

29. The instrument defined in claim 21, further comprising additional storing means in said frame means for holding additional staples, loading means for shifting said additional staples from said additional storing means into said cartridge, and staple arrest means for preventing motion of said additional staples during a cartridge rotation operation and said stapling operation.

30. The instrument defined in claim 29 wherein said additional storing means includes an elongate chamber in said frame means and wherein said loading means includes a compression spring.

31. The instrument defined in claim 30 wherein said staple forming and ejection means includes an elongate plate element movably mounted to said frame means and wherein said staple arrest means includes a catch member pivotably mounted to said frame means, said timing means including a slot formed in said elongate plate element and a pin on said rotator member coacting with said slot, said catch member having a camming portion engageable with said plate element.

32. The instrument defined in claim 17 wherein said staple forming and ejection means includes an anvil member with an anvil flange projecting, during said stapling operation, into a staple forming plane intersecting said cartridge, further comprising shifting means for moving said anvil flange transversely away from said staple forming plane prior to a cartridge rotation operation.

33. The instrument defined in claim 32 wherein said staple forming and ejection means includes an elongate plate element movably mounted to said frame means, said anvil member being an elongate member with a proximal end attached to said frame means and a distal end carrying said anvil flange, said shifting means including a camming projection on said anvil member engageable with said plate member.

34. The instrument defined in claim 17, further comprising additional storing means in said frame means for holding additional staples, loading means for shifting said additional staples from said additional storing means into said cartridge, and staple arrest means for preventing motion of said additional staples during a cartridge rotation operation and said stapling operation.

35. The instrument defined in claim 34 wherein said additional storing means includes an elongate chamber in said frame means and wherein said loading means includes a compression spring.

36. The instrument defined in claim 34 wherein said staple forming and ejection means includes an elongate plate element movably mounted to said frame means and wherein said staple arrest means includes a catch member pivotably mounted to said frame means, said catch member having a camming portion engageable with said plate element.

37. The instrument defined in claim 17 wherein said staple forming and ejection means includes an anvil member with an anvil flange projecting, during said stapling operation, into a staple forming plane intersecting said cartridge, further comprising (a) shifting means for moving said anvil flange transversely away from said staple forming plane prior to a cartridge rotation operation, (b) additional storing means in said frame means for holding additional staples, (c) loading means for shifting said additional staples from said additional storing means into said cartridge, (d) staple arrest means for preventing motion of said additional staples during a cartridge rotation operation and said stapling operation, and (e) timing means for timing rotation of said cartridge, shifting of said anvil flange and operation of said staple arrest means.

38. The instrument defined in claim 37 wherein said staple arrest means includes a catch member pivotably mounted to said frame means, said timing means includes (a) an elongate plate element movably mounted to said frame means, (b) a camming projection on said anvil member engageable with said plate element, (c) a camming portion of said catch member engageable with said plate element, and (d) a rotator member slidably mounted to said frame means and a slot formed in said plate element coating with a pin on said rotator member.

39. The instrument defined in claim 37 wherein said plate element is connected to said frame means by a biasing spring.

40. The surgical instrument of claim 17 further comprising an anvil member having a camming projection thereon which engages said staple forming plate during a forward or distal motion thereof and thereby cooperates with that plate member to laterally bend said anvil member, said anvil member being removed, during a cartridge rotation, from engagement with said cartridge.

41. A surgical instrument for suturing an opening in internal body tissues of a patient from inside a body cavity of the patient, said instrument comprising:
elongate frame means for providing a superstructure for said instrument;
staple storing means on said frame means for temporarily storing at least one staple, said staple storing means including an elongate staple cartridge rotatably mounted to said frame means at a distal end thereof;
rotator means mounted to said frame means and operatively connected to said cartridge for rotating said cartridge from an orientation aligned with said frame means to a staple ejection orientation transverse to said frame means; and
staple forming and ejection means at least in part movably mounted to said frame means for ejecting said staple from said stable storing means into the body tissues of the patient upon the termination of a rotation operation and deforming said staple from an open position to a closed position in which said staple holds together two pieces of body tissue on opposite sides of said opening.

42. The instrument defined in claim 41 including tissue positioning means on said frame means for gripping, approximating and holding in stapling position said two pieces of body tissue prior to and during a stapling operation.

43. The instrument defined in claim 42 wherein said tissue positioning means is separate and distinct from said staple forming and ejection means.

44. The instrument defined in claim 43 wherein said instrument includes a distal end adjacent which at least part of said staple forming and ejection means are exposed from said frame means, said instrument also including a proximal end and means mounted to said frame means for sealing fluid-tight said distal end of said instrument from said proximal end of said instrument.

45. The instrument defined in claim 41 wherein said cartridge includes a staple chamber and means including spring tines for preventing a staple from falling out of said chamber prior to a staple ejection operation.

46. The instrument defined in claim 45 wherein said cartridge is provided with means for receiving and storing additional staples subsequently to said stapling operation, said means for receiving and storing including an inlet opening, a biasing spring and a staple plate.

47. The instrument defined in claim 41 wherein said rotator means includes a rotator member slidably mounted to said frame means for longitudinal motion therealong and a rotator link pivotably attached at one end to said cartridge and at an opposite end to said rotator member.

48. The instrument defined in claim 47, further comprising timing means mounted to said frame means for controlling the initation and duration of motion of said rotator member.

49. The instrument defined in claim 48 wherein said staple forming and ejection means includes an elongate plate element movably mounted to said frame means, said timing means including a slot formed in said elongate plate element and a pin on said rotator member coacting with said slot.

50. The instrument defined in claim 49 wherein said rotator means further includes spring biasing means for forcing said pin against said elongate plate element.

51. The instrument defined in claim 50, further comprising stop means including coacting elements on said rotator member and said frame means for limiting a range of longitudinal motion of said rotator member and concomitantly limiting a range of rotational motion of said cartridge.

52. The instrument defined in claim 51, wherein said slot is provided with beveled ends and said pin is formed with a substantially conically shaped free end, whereby said pin is compelled to moved transversely out of said slot upon an arresting of longitudinal motion of said rotator member by said stop means.

53. The instrument defined in claim 51 wherein said stop means includes a floating pin slidably mounted to said frame means for controlled movement in a direction transverse thereto, a shoulder at a proximal end of said rotator member and an additional slot in said elongate plate element, said additional slot being formed with a beveled proximal end and said floating pin being provided with conically shaped ends, whereby said floating pin is forced in a camming type motion transversely out of said slot upon an engagement of said floating pin with said beveled proximal end during relative motion of said elongate plate element and said rotator member after termination of a cartridge rotation operation and is simultaneously moved into a locking engagement with said shoulder.

54. The instrument defined in claim 48 wherein said staple forming and ejection means includes an anvil member with an anvil flange projecting, during said stapling operation, into a staple forming plane intersecting said cartridge, further comprising shifting means for moving said anvil flange transversely away from said staple forming plane prior to a cartridge rotation operation.

55. The instrument defined in claim 54 wherein said staple forming and ejection means includes an elongate plate element movably mounted to said frame means, said timing means including a slot formed in said elongate plate element and a pin on said rotator member coacting with said slot, said anvil member being an elongate member with a proximal end attached to said frame means and a distal end carrying said anvil flange, said shifting means including a camming projection on said anvil member engageable with said plate member.

56. The instrument defined in claim 48, further comprising additional storing means in said frame means for holding additional staples, loading means for shifting said additional staples from said additional storing means into said cartridge, and staple arrest means for preventing motion of said additional staples during a cartridge rotation operation and said stapling operation.

57. The instrument defined in claim 56 wherein said additional storing means includes an elongate chamber in said frame means and wherein said loading means includes a compression spring.

58. The instrument defined in claim 57 wherein said staple forming and ejection means includes an elongate plate element movably mounted to said frame means and wherein said staple arrest means includes a catch member pivotably mounted to said frame means, said timing means including a slot formed in said elongate plate element and a pin on said rotator member coacting with said slot, said catch member having a camming portion engageable with said plate element.

* * * * *